US007598371B2

(12) United States Patent
Willson et al.

(10) Patent No.: US 7,598,371 B2
(45) Date of Patent: Oct. 6, 2009

(54) NUCLEIC ACID SEPARATION USING IMMOBILIZED METAL AFFINITY CHROMATOGRAPHY

(75) Inventors: Richard C. Willson, Houston, TX (US); Jason C. Murphy, North Wales, PA (US)

(73) Assignee: University of Houston, Houston, TX (US)

( * ) Notice: Subject to any disclaimer, the term of this patent is extended or adjusted under 35 U.S.C. 154(b) by 581 days.

(21) Appl. No.: 09/994,701

(22) Filed: Nov. 6, 2001

(65) Prior Publication Data
US 2004/0152076 A1 Aug. 5, 2004

Related U.S. Application Data

(60) Provisional application No. 60/246,292, filed on Nov. 6, 2000.

(51) Int. Cl.
*C07H 21/00* (2006.01)
*G01N 30/02* (2006.01)
*B01D 15/08* (2006.01)

(52) U.S. Cl. .................. 536/25.4; 436/161; 422/70; 210/656

(58) Field of Classification Search .................. 435/6; 514/49, 45; 536/26.23
See application file for complete search history.

(56) References Cited

U.S. PATENT DOCUMENTS 6,180,778 B1 * 1/2001 Bastian et al. ............. 536/25.4

FOREIGN PATENT DOCUMENTS

WO      WO 98 00435        1/1998

OTHER PUBLICATIONS

Petty KJ, Metal-Chelate Affinity Chromatography, in Current Protocols in Molecular Biology, John Wiley & Sons, Inc, 2000 (article first published 1996), pp. 10.11.10-10.11.24.*
Yarchoan R et. al, Administration of 3'-azido-3'-deoxythymidine, an inhibitor of HTLV-III/LAV replication, to patients with AIDS or AIDS-related complex, Lancet, 1986, 1(8481):575-580.*
Yarchoan R, Mitsuya H, Thomas RV, Pluda JM, Hartman NR, Perno C-F, Marczyk KS, Allain J-P, Johns DG, Broder S, In ivo activity against HIV nd favorable toxicity profile of 2',3'-dideoxyinosine, Science, 1989, 245:412-415.*
Alberts B, Bray D, Lewis J, Raff M, Roberts K, Watson JD, Molecular Biology of the Cell, third editionGarland Publishing, Inc. 1994, p. 68.*
Min, C. et al., "Immobilized metal affinity chromatography of DNA", Nucleic acids Res., 1996, vol. 24: pp. 3806-3810.*
Willson, Richard C. Et. al., Immobilized-metal affinity separation of nucleic acids. Abstracts of Papers America Chemcical Society vol. 221, No. 1-2, 2001 p. BIOT 89 XPO08013459.
Fanou-AYI; et. al. Metal-chelate affinity chromatography as a separation tool. Annals of the New York Academy of Science United States 1983. vol. 413, 1983, pp. 300-306, XP008013296.
Hubert P. et. al. Metal Chelate Affinity Chromatography; 1. Influence of Various Parameters on the Retention of Nucleotides and Related Compounds. Journal of Chromatography, vol. 198, No. 3, 1980, pp. 247-256. XP001109605.
Hubert P, et. al. Metal Chelate Affinity Chromatography 2. Group Separation of Mono Nucleotides and DI Nucleotides. Journal of Chromatography vol./ 206, No. 1, 1981, pp. 164-168, XP001109604.
Kothari RM; Fractionation of DNA on a Metal ION Equilibrated Cation Exchanges Part 1 Chromatographic Profiles of DNA on An IR-120 Aluminum ION Column. Journal of Chromatography. vol. 52, No. 1, 1970, pp. 119-129.XP008013369.
Kothari RM; Some aspects of Fractionation of DNA on an IR-120 Trivalent Aluminum Column Part 2 Effect of the Physical State of DNA on Chromatographic Profiles. Journal of Chromatography, vol. 53, No. 3, 1970, pp. 580-583. XP001109612.
Gruenwedel DW, et. al. Mercurated Dextram Column Chromatography For Fractionating Mono Nucleotides. Proceedings of the National Acadmey of Sciences of the United States. vol. 68, No. 9, 1971, pp. 2002-2005. XP008013376.
Dobrowolska, G, et.al., Model Studies on Iron-II Ion Affinity Chromatography Interaction of Immobilized Metal Ions with Nucleotides. Journal of Chromatography, vol. 541, No. 1-2, 1991, pp. 333-340 XP008013339.
Holmes, Leonard D. et. al. Immobilized iron (III) metal affinity chromatography for the separation of phosphorylated macromolecules; Ligands and applications . Journal of Liquid Chromatography & Related Technologies, vol. 20, No. 1, 1997, pp. 123-142. XP008013292.
Ferreira GNM, et. al. Downstream Processing of plasmid DNA for gene therapy and DNA vaccine applications. Trends in Biotechnology vol. 18, No. 9 Sep. 1, 2000 pp. 380-388, XP004214265.

* cited by examiner

*Primary Examiner*—Michael Burkhart
(74) *Attorney, Agent, or Firm*—Richard Coale Willson, Jr; Robert W. Strozier

(57) ABSTRACT

An immobilized metal affinity chromatography (IMAC) method for separating and/or purifying compounds containing a non-shielded purine or pyrimidine moiety or group such as nucleic acid, presumably through interaction with the abundant aromatic nitrogen atoms in the purine or pyrimidine moiety. The method can also be used to purify compounds containing purine or pyrimidine moieties where the purine and pyrimidine moieties are shielded from interaction with the column matrix from compounds containing a non-shielded purine or pyrimidine moiety or group. Thus, double-stranded plasmid and genomic DNA, which has no low binding affinity can be easily separated from RNA and/or oligonucleotides which bind strongly to metal-charged chelating matrices. IMAC columns clarify plasmid DNA from bacterial alkaline lysates, purify a ribozyme, and remove primers and other contaminants from PCR reactions. The metal ion affinity of yeast RNA decreases in the order: copper (II), nickel (II), zinc (II), and cobalt (II).

25 Claims, 14 Drawing Sheets

NUCLEIC ACID SEPARATION USING IMMOBILIZED METAL AFFINITY CHROMATOGRAPHY

RELATED APPLICATIONS

This application claims provisional priority to U.S. Provisional Patent Application Serial No. 60/246,292 filed Nov. 6, 2000.

GOVERNMENT LICENSE RIGHTS STATEMENT

The U.S. Government has a paid-up license in this invention and the right in limited circumstances to require the patent owner to license others on reasonable terms as provided for by the terms of grant No. R825354-01-0 from the National Space Biomedical Research Institute and the Environmental Protection Agency.

BACKGROUND OF THE INVENTION

1. Field of the Invention

The present invention relates to an immobilized metal affinity chromatography (IMAC) instrument, a substrate containing immobilized metal affinity ligands, and a method for purifying and/or separating compounds containing a non-shielded purine or pyrimidine moiety or group using the instrument or substrate.

More particularly, the present invention relates to an immobilized metal affinity chromatography (IMAC) instrument and/or a substrate containing immobilized metal affinity ligands where the metal ion immobilized on the ligand of the column of an IMAC instrument or the substrate is capable of binding compounds containing a non-shielded purine or pyrimidine moiety or group where binding affinities results in a separation of different compounds containing a non-shielded purine or pyrimidine moiety or group or in a purification of compounds that do not contain a non-shielded purine or pyrimidine moiety or group from compounds that do contain a non-shielded purine or pyrimidine moiety or group. The present invention also relates to a method for purifying and/or separating compounds containing a non-shielded purine or pyrimidine moiety or group such as single stranded DNA, RNA, or other compounds containing a non-shielded purine or pyrimidine moiety or group, or to a method for removing compounds containing a non-shielded purine or pyrimidine moiety or group from compounds that do not contain a non-shielded purine or pyrimidine moiety or group such as removing nucleotides and primers from PCR reactions and/or reaction products and purifying plasmid DNA.

2. Description of the Related Art

Immobilized Metal Affinity Chromatography (IMAC) was introduced by Porath et al. (1, 2) as a means of purifying proteins based on the affinity of their surface-exposed amino acids (especially histidines) for chelated metal ions. The method has found widespread application in the purification of recombinant histidine-tagged and pharmaceutical proteins, most commonly using Cu(II) and Ni(II) ions chelated by iminodiacetic acid (IDA) and nitrilotriacetic acid (NTA) functionalities. Metal chelate ligands are best known as affinity agents in chromatography but have also been immobilized on foams (3), membranes (4), biosensor chips (5), and in electrophoresis gels (6); they have also been used as affinity precipitation agents (7).

The interaction of metal ions with nucleic acids is a long-standing and active field of study (8, 9). While metal ion binding to nucleic acids is well known, and plays an important role in the function of the widely used cancer drug cisplatin (10), IMAC has found very limited application in the purification of nucleic acids. Fanou-Ayi and Vijayalakshmi (11) and Hubert and Porath (12) demonstrated the binding of mononucleotides to copper IMAC resins, and histidine-conjugated PCR primers have been used to facilitate purification of the resulting histidine-tagged oligonucleotide products (13), but the potential applications of IMAC in nucleic acid separation and analysis remain largely unexplored.

Thus, there is a need in the art for an IMAC instrument and method, where the IMAC column includes metals or metal ions capable of binding compounds containing a non-shielded purine or pyrimidine moiety or group to effectuate separation and/or purification of different compounds containing a non-shielded purine or pyrimidine moiety or group or for purifying compounds that do not contain a non-shielded purine or pyrimidine moiety or group from compounds that do contain a non-shielded purine or pyrimidine moiety or group.

SUMMARY OF THE INVENTION

The present invention provides a composition including a first molecular component having immobilized metal atoms and/or ions and a second molecular component including a non-shielded purine moiety or group and/or pyrimidine moiety or group, where the second molecular component is bound to, associated with and/or interacting with the metal atoms and/or ions of first molecular component.

The present invention provides a composition including a molecular component having immobilized metal atoms and/or ions capable of associating with, interacting with or binding a second molecular component including a non-shielded purine moiety or group and/or pyrimidine moiety or group.

The present invention provides an immobilized metal affinity composition including a molecular component including immobilized metal atoms and/or ions capable of binding compounds including a non-shielded purine moiety or group and/or pyrimidine moiety or group.

The present invention provides an immobilized metal affinity composition including a molecular component including immobilized metal atoms and/or ions capable of binding compounds including a non-shielded purine moiety or group and/or pyrimidine moiety or group and a compound including a non-shielded purine moiety or group and/or pyrimidine moiety or group bound thereto.

The present invention provides an immobilized metal affinity chromatography (IMAC) column including a matrix or absorbent having immobilized metal atoms and/or ions capable of binding compounds containing a non-shielded purine moiety or group and/or pyrimidine moiety or group.

The present invention provides an immobilized metal affinity chromatography (IMAC) column including a matrix or absorbent having immobilized metal atoms and/or ions capable of binding compounds containing a non-shielded purine moiety or group and/or pyrimidine moiety and/or group and a compound containing a non-shielded purine moiety or group and/or pyrimidine moiety or group bound thereto.

The present invention provides a surface including an immobilized metal affinity composition coated thereon, where the composition includes immobilized metal atoms and/or ions capable of binding compounds containing a non-shielded purine moiety or group and/or pyrimidine moiety or group.

The present invention provides a surface including an immobilized metal affinity composition coated thereon, where the composition includes immobilized metal atoms and/or ions capable of binding compounds containing a non-shielded purine moiety or group and/or pyrimidine moiety or group, and a compound containing a non-shielded purine moiety or group and/or pyrimidine moiety or group bound thereto.

The present invention provides a method for separating different compounds containing a non-shielded purine moiety or group and/or a pyrimidine moiety or group by passing a solution containing the different compounds through an immobilized metal affinity chromatography (IMAC) column including immobilized metal atoms and/or ions capable of binding compounds containing a non-shielded purine moiety or group and/or pyrimidine moiety or group and analyzing the effluent from the column as a function of time or over a given period of time.

The present invention provides a method for purifying a solution comprising a major compound having one or more (at least one) shielded purine moiety or group or pyrimidine moiety or group and a minor compound containing one or more (at least one) non-shielded purine moiety or group or pyrimidine moiety or group by passing the solution through an immobilized metal affinity chromatography (IMAC) column including a matrix having immobilized metal atoms and/or ions capable of binding compounds containing one or more (at least one) non-shielded purine moiety or group or pyrimidine moiety or group and analyzing the effluent from the column as a function of time or over a given period of time. The column can include metal atoms and/or ions that have a higher or lower binding affinity for the major verses the minor compound and separation will result, provided that the binding affinities are indeed different.

The present invention provides a method for purifying a solution containing a compound that does not contain a non-shielded purine moiety or group or pyrimidine moiety or group and a compound that does contain a (or a plurality of) non-shielded purine moiety(ies) or group(s) and/or a (or a plurality of) pyrimidine moiety(ies) or group(s) by passing the solution through an immobilized metal affinity chromatography (IMAC) column including immobilized metal atoms or ions capable of binding compounds containing a non-shielded purine moiety or group and/or pyrimidine moiety or group and analyzing the effluent from the column as a function of time or over a given period of time.

The present invention also provides a method including the steps of contacting a mixture including components having shielded one or more purine and/or pyrimidine moieties and components having non-shielded one or more purine and/or pyrimidine moieties with a molecular component including immobilized metal atoms and/or ions capable of binding the components having one or more non-shielded purine and/or pyrimidine moieties and eluting the components having one or more shielded purine and/or pyrimidine moieties.

The present invention also provides a method including the steps of contacting a mixture of components having non-shielded one or more purine and/or pyrimidine moieties with a molecular component including immobilized metal atoms and/or ions capable of binding the components having one or more non-shielded purine and/or pyrimidine moieties to form an associated mixture and flowing a solution over the associated mixture to affect a partial or complete separation of components.

The present invention also provides a composition comprising a polymeric material including immobilized metal atoms and/or ions and a compound having a non-shielded purine and/or pyrimidine moiety or group bound thereto, where the compound is selected from the group of mRNA, RNA, ribosomyl DNA, denatured DNA, denatured cDNA, and other biological molecules having a purine and/or pyrimidine moiety or group.

The present invention also provides an immobilized metal affinity composition comprising immobilized metal atoms or ions capable of binding compounds containing a non-shielded purine or pyrimidine moiety or group and a compound containing a non-shielded purine or pyrimidine moiety or group bound thereto, where the compound is selected from the group of mRNA, RNA, ribosomyl DNA, denatured DNA, denature cDNA, and other biological molecules having a purine and/or pyrimidine moiety or group.

The present invention also provides an immobilized metal affinity chromatography (IMAC) column comprising immobilized metal atoms or ions capable of binding compounds containing a non-shielded purine or pyrimidine moiety or group and a compound containing a non-shielded purine or pyrimidine moiety or group bound thereto, where the compound is selected from the group of mRNA, RNA, ribosomyl DNA, denatured DNA, denature cDNA, and other biological molecules having a purine and/or pyrimidine moiety or group.

The present invention also provides a surface comprising an immobilized metal affinity composition coated thereon, where the composition includes immobilized metal atoms or ions capable of binding compounds containing a non-shielded purine or pyrimidine moiety or group, and a compound containing a non-shielded purine or pyrimidine moiety or group bound thereto, where the compound is selected from the group of mRNA, RNA, ribosomyl DNA, denatured DNA, denature cDNA, and other biological molecules having a purine and/or pyrimidine moiety or group.

The present invention also provides a multisubstrate column comprising a first zone comprising an IMAC ligand or matrix and a second zone comprising another separation medium, where the IMAC, which is relatively insensitive to an ionic strength of a solution, binds compounds comprising non-shielded purine or pyrimidine moieties or groups and the second zone is designed to separate other constituents of the solution based on the other constituents interaction with the stationary material of the second zone. The first zone is followed by or is preceded by the second zone. Preferably, the second zone follows the first zone, where the second zone comprises non-metal contain IMAC substrate for binding any leached metal ions from the first zone. Alternatively, the second zone comprises an anion exchange material or HIC material. Preferably, the column is made using monolith technology.

The present invention also provides an IMAC pre-filters for purifying solution containing large quantities of plasmid.

The present invention also provides an IMAC ligand or matrices deposited on capillary walls or in solution, where the IMAC ligand or matrix would alter the retention times of compounds having non-shielded purine and/or pyrimidine moieties in capillary electrophoresis. Preferably, the solution comprises an IMAC ligand or matrix bonded to, associated with or deposited on substrate. Preferably, the substrate is a polymer or dendrimer. Preferably, the polymer is a PEG.

The present invention also provides an IMAC ligand or matrices deposited on a surface or in a gel, where the IMAC ligand or matrix alters retention times for of compounds having non-shielded purine and/or pyrimidine moieties in slab gel electrophoresis or alters in traditional IMAC chromatography.

The present invention also provides a plasmid separation technique using membranes coated with or impregnated with an IMAC matrix to filter out or prevent free RNA from migrating to the other side of the membrane structure.

The present invention also provides a porous stirrer (a stick-like rod) with an IMAC ligand deposited thereon or therein to batch bind RNA from a solution containing plasmids to clarify plasmid lysate.

The present invention also provides an assay using IMAC matrices deposited in the wells of microplates and then bind a single stranded oligonucleotide having a fluorescent tag to the matrix, where the IMAC matrix either contains a quencher in close proximity to the metal binding sites or the substrate upon which the IMAC is coated acts as a fluorescent quencher and when a complimentary sequence is added to a well containing the fluorescent tagged oligonucleotide, the two pair and the paired sequence is released and the tag fluoresces.

The present invention also provides an assay comprising the steps of contacting a microplate substrate comprising wells coated with a composition comprising an IMAC ligand with a single stranded oligonucleotide including a first molecular and/or atom tag to form a IMAC-oligonucleotide complex, contacting a nucleic acid sequence including a second molecular and/or atomic tag with the IMAC-oligonucleotide complex, and measuring a fluorescence of the resulting mixtures, where the tags interact to produce a fluorescent pair or a non-fluorescent pair if the nucleic acid sequence includes a complimentary subsequence to oligonucleotide and where pair results in release of the paired nucleic acid sequence and oligonucleotide.

The present invention also provides an assay comprising the steps of contacting a substrate comprising a surface coated with a composition comprising an IMAC ligand and a first fluorophore with an oligonucleotide including a second fluorophore and measuring an effective Stoke shift such that a large effective Stoke shift signifies oligonucleotide binding to the coated substrate and a normal effective Stoke shift signifies no oligonucleotide binding to the coated substrate.

The present invention also provides a method for separating different compounds containing a non-shielded purine or pyrimidine moiety or group by passing a solution containing the different compounds through an immobilized metal affinity chromatography (IMAC) comprising immobilized metal atoms or ions capable of binding compounds containing a non-shielded purine or pyrimidine moiety or group and analyzing the effluent from the column as a function of time or over a given period of time.

The present invention also provides a method for purifying a solution containing a major compound containing a non-shielded purine or pyrimidine moiety or group and a minor compound containing a non-shielded purine or pyrimidine moiety or group by passing the solution through an immobilized metal affinity chromatography (IMAC) comprising immobilized metal atoms or ions capable of binding compounds containing a non-shielded purine or pyrimidine moiety or group and analyzing the effluent from the column as a function of time or over a given period of time. The column can include metal atoms or ions that have a higher or lower binding affinity for the major verses the minor compound and separation will results, provided that the binding affinities are indeed different.

The present invention also provides a method for purifying a solution containing a compound that does not contain a non-shielded purine or pyrimidine moiety or group and a compound that does contain a non-shielded purine or pyrimidine moiety or group by passing the solution through an immobilized metal affinity chromatography (IMAC) comprising immobilized metal atoms or ions capable of binding compounds containing a non-shielded purine or pyrimidine moiety or group and analyzing the effluent from the column as a function of time or over a given period of time.

The present invention also provides a method for removing fluorophore tagged nucleotides or nucleosides from a solution involving passing the solution through an IMAC column capable of either binding to nitrogen atoms of a base residue in the nucleotides or nucleoside, binding to atoms and/or functional groups of the fluorophores or both and removing all non-bound materials from the column resulting in the removal of fluorophore labeled nucleotides or oligonucleotides from the solution.

The present invention also provides a method for making multisubstrate columns comprising running a small amount of IMAC ligand onto an activated column and then flooding the rest of the column with one or more additional ligands or stationary phases.

The present invention also provides a method for separating compounds comprising the steps of: (a) passing a solution comprising a mixture of compounds including a non-shielded purine or pyrimidine moiety or group through a column including an interior surface coated with an immobilized metal affinity composition comprising a matrix and immobilized metal ions capable of binding compounds containing a non-shielded purine or pyrimidine moiety or group; (b) analyzing the effluent from the column as a function of time for each compound; and (c) collecting more purified samples of each compound.

The present invention also provides a method for separating compounds comprising the steps of: (a) passing a solution comprising a mixture of compounds including a non-shielded purine or pyrimidine moiety or group through a column including an interior surface coated with an immobilized metal affinity composition comprising a matrix and immobilized metal ions capable of binding compounds containing a non-shielded purine or pyrimidine moiety or group; (b) detecting the present of each compound in an effluent from the column as a function of time from detectable properties of each compound; and (c) determining the identity of each compound from the detected properties.

The present invention also provides a method for separating compounds comprising the steps of: (a) contacting a solution comprising a first compound including a non-shielded purine or pyrimidine moiety or group and a second compound including no non-shielded purine or pyrimidine moieties or groups with an immobilized metal affinity composition comprising a matrix and immobilized metal ions capable of binding compounds containing a non-shielded purine or pyrimidine moiety or group; and (b) washing the second compound from the matrix to form a more purified second compound.

The present invention also provides a method for separating compounds comprising the steps of: (a) passing a solution comprising a first compound including a non-shielded purine or pyrimidine moiety or group and a second compound including no non-shielded purine or pyrimidine moieties or groups through a column coated with an immobilized metal affinity composition comprising a matrix and immobilized metal ions capable of binding compounds containing a non-shielded purine or pyrimidine moiety or group; and (b) collecting the second compound in a more purified state.

The present invention also provides a method for separating compounds comprising the steps of: (a) passing a solution comprising a first compound including a non-shielded purine or pyrimidine moiety or group and a second compound including no non-shielded purine or pyrimidine moieties or groups over a surface coated with an immobilized metal affinity composition comprising a matrix and immobilized metal ions capable of binding compounds containing a non-shielded purine or pyrimidine moiety or group; and (b) collecting the second compound in a more purified state.

The present invention also provides a method for purifying a solution containing a major compound containing a non-shielded purine or pyrimidine moiety or group and a minor compound containing a non-shielded purine or pyrimidine moiety or group by passing the solution through an immobilized metal affinity chromatography (IMAC) including immobilized metal atoms or ions capable of binding compounds containing a non-shielded purine or pyrimidine moiety or group and analyzing the effluent from the column as a function of time or over a given period of time. The column can include metal atoms or ions that have a higher or lower binding affinity for the major verses the minor compound and separation will results, provided that the binding affinities are indeed different.

The present invention also provides a method for purifying a solution containing a compound that does not contain a non-shielded purine or pyrimidine moiety or group and a compound that does contain a non-shielded purine or pyrimidine moiety or group by passing the solution through an immobilized metal affinity chromatography (IMAC) including immobilized metal atoms or ions capable of binding compounds containing a non-shielded purine or pyrimidine moiety or group and analyzing the effluent from the column as a function of time or over a given period of time.

The present invention also provides a method for separating poly(A) tailed mRNA from eukaryotic cells comprising the step of passing a solution containing eukaryotic cell mRNA through an IMAC column or over an IMAC matrix and separating poly(A) tailed mRNA from other mRNA, where the poly(A) tailed mRNA elutes from the IMAC matrix last because the poly(A) tail has such a high affinity for IMAC matrix, where the poly(A) tails are usually 50-200 bases long.

The present invention also provides a method for separating denatured nucleic acid sequences having A rich regions from the complementary stranded having T rich regions comprising contacting a solution containing the sequences having A rich regions with an IMAC matrix or ligand and separating all unbound components in the solution and collecting the sequences having A rich regions.

The present invention also provides a method for separating denatured nucleic acid sequences having C rich regions from the complementary stranded having G rich regions comprising contacting a solution containing the sequences having C rich regions with an IMAC matrix or ligand and separating all unbound components in the solution and collecting the sequences having C rich regions.

The present invention also provides a method for separating denatured nucleic acid sequences having A-C, A-G, and/or A-C-G rich regions from the complementary stranded having T-G, T-C and or T-G-C rich regions comprising contacting a solution containing the sequences having A-C, A-G, and/or A-C-G rich regions with an IMAC matrix or ligand and separating all unbound components in the solution and collecting the sequences having A-C, A-G, and/or A-C-G rich regions.

The present invention also provides a method for purifying food stuffs containing purine and/or pyrimidine moieties comprising the steps of: (a) forming a crude food stuff comprising cellular constituents including digestable proteins and nucleic acid contaminants; (b) contacting the food stuff with an agent including an IMAC ligand coordinating a metal atom and/or ion capable of binding contaminants including a non-shielded purine or pyrimidine moiety to form an IMAC-contaminant composition; and (c) separating the IMAC-contaminant composition from the crude food stuff to produce a purified food stuff. Further, the method includes the step of treating the crude food stuff with a DNASE, endo or exo nuclease or other nucleic acid digestion enzyme or agent prior to the contacting step.

The present invention also provides a method for purifying a crude compound containing a non-shielded purine and/or pyrimidine moiety comprising the steps of: (a) forming a crude mixture comprising a desired compound and acid contaminants; (b) contacting the crude mixture with an agent including an IMAC ligand coordinating a metal atom and/or ion capable of binding to the desired compound to form an IMAC-compound complex; (c) separating the complex from the contaminants; and (d) recovering the compound from the complex. Preferably, the compound is an AIDs drugs, co-enzyme A, or the like. The preferred AIDs drugs include AZT or DDI.

Preferably, the interactions between the metal atoms and/or ions and the non-shielded purine and/or pyrimidine are reversible.

Tabulation of Applications and Preferences

TABLE A

| Parameter | Units/ | Preferred | More Prefer. | Most Pref. |
|---|---|---|---|---|
| Product purity | % | 95-100 | 99-100 | 99.99 |
| RNA in DNA | % of ppt. | 0-10 | 0-2 | 0-1 |
| DNA Product | Type | pDNA, mDNA, cDNA, oDNA, genomic DNA, Primer, Oligonucleotide, mRNA, PCR products A-tailed PCR products, polyA mRNA, RNA-reduced solution, DNA-reduced solution, Nucleotide-reduced solution, Plasmid DNA with reduced content of nicked and linearized forms, Double-stranded hybrids | pDNA, mRNA, genomic DNA, oligonucleotides | pDNA |

TABLE A-continued

| Parameter | Units/ | Preferred | More Prefer. | Most Pref. |
|---|---|---|---|---|
| Column Temperature for Separation | ° C. | 0-120 | 5-50 | 15-25 |
| Metals | Metal | Cu(II), Ni(II), Zn(II), Co(II), Sc(II), Ti(II), V(II), Cr(II), Mn(II), Fe(II) | Cu(II), Ni(II) | Cu(II) |
| NonShielded | Groups | Bases in single-stranded nucleic acids with 1-5,000,000 bases | Bases in single-stranded nucleic acids with 4-50,000 bases | Bases in single-stranded nucleic acids with 10-5,000 bases |
| Purines | Compounds | Adenine, guanine NN need more non-nucleic acid examplesNN | Adenine, guanine | adenine |
| Pyrimidines | Compounds | Cytosine, thymine, uracil | | |
| Support Material | type | Agarose, acrylamide, silica, other polymers, "Smart polymer" Silica, silicon, glass, dextran, polystyrene, phase-separating polymer bearing chelator | Agarose, silica | agarose |
| Column Volume | cc/g product | 1 to 100,000 | 10-1,000 | 100 |
| Space Velocity | Vol/Vol/Hr. | NNN 0-infinite (for non-flow applications, or zero-volume layers of adsorbent) | 1-1,000 | 5 |
| Support Shape | Shape | Beads, cut pellets, well plate, monolith, filter, membrane, tube, spin column, MEMS device, magnetic particles, thermo- or salt-precipitable polymer, phase-partitioning polymer, soluble chelating polymer | Beads, magnetic particles, well plate | beads |
| Metal Concentration | μmol/ml Matrix | 10-100 | 30-100 | 50-100 |
| Binding Affinity | Major:minor compound | 1.001 to 10000000 | 3 to 10,000 | 30 |
| Fluorophores | Com'd, Mfger | Fluorescein, Texas Red, Cy3, Cy5, rhodamine, ALEXA dyes, quantum dot | Fluorescein, Cy5, Cy3, ALEXA dyes | Fluorescein |
| Fluorophores Conc. | g/liter | 1 fM-1 M | 1 nM-1 mM | 50 uM |
| Nucleotides | Compounds | A, G, C, T, I | A, G | A |
| Nucleosides | Compounds | A, G, C, T, I | A, G | A |
| 2nd Zone Other Constituents | Compounds | Hydrophobic Interaction Chromatography, Ion Exchange, Hydroxyapatite, Fe(II) IMAC, Butyl Agarose, Reverse Phase Resin, Zirconia | | |
| Other surfaces for IMAC Ligand | Area | Filter, mesh, frit, adsorbent, coating on column wall, coating on tubing wall, coating on tank or container wall | frit, adsorbent, coating on column wall | Adsorbent coating on wall |
| HIC/Ion exch. Material | Type | Butyl, phenyl, amine, Quaternary amine, DEAE, C18 (reverse phase) | Quaternary amine, DEAE | Quaternary amine |
| Monoliths | Shape | Rod, chip, disk, hollow tube | Disk, rod | disk |
| IMAC Ligands | Ligands | Iminodiacetic acid (IDA), Nitrilotriacetic acid (NTA), Pentadentate chelator (PDC), tris-(2-ethylaminoethyl) amine (TREN), dipicolyl amine (DPA), chelating lipids | IDA, NTA | IDA |
| Prefilters | Type | Spin, precoat, RNA removal | | |
| Matrix | Composition | Polymer with chelating groups, NTA agarose, IDA on acrylamide polymer, chelating silane derivatives on silica | | |
| Detectors | Type | Flow absorbance detector, flow fluorescence detector, flow electrochemical detector, Spectrometer, GLC, fluorometer, fluorescence imaging, Mass | | |

TABLE A-continued

| Parameter | Units/ | Preferred | More Prefer. | Most Pref. |
|---|---|---|---|---|
| | | Spectrometer, plasmon resonance, microbalance, electrode | | |
| Washing Fluid | Composition | Water, ethanol, polyethylene glycol, purine solution, imidazole, ammonium chloride, histidine, AMP, ADP, ATP, GTP, GDP, GMP, Guanine, Adenosine, competitive eluant, base, acid, amine | | |
| Membranes | Type, Mfger | Semi-permeable membranes with IMAC Ligands attached[a,b] | | |
| Comp'd w/o non shielded Purine/Pyrimidine | Structure | Structured plasmid DNA, gDNA Structured RNA (some types) Defect-free PCR product, RNA/DNA hybrid | Plasmid DNA, Defect-free PCR product | Plasmid DNA |
| Comp'd With non shielded Purine/Pyrimidine | Compounds | Denatured plasmid DNA, Denatured gDNA mRNA Defect-containing PCR product, PCR product with extra overhang, RNA in alkaline lysate, RNA/DNA hybrid, sequencing ladder, primer, nucleotide, mismatch-containing duplex | mRNA, PCR products with defects, RNA in alkaline lysate, primer | RNA, primer |
| Poly A Tail Length | Bases | 1-1000 | 50-200 | 100 |
| A Rich Region | Compounds | PolyA, mRNA | | |
| T Rich Region | Compounds | PolyT, mRNA | | |
| G Rich Region | Compounds | PolyG, mRNA | | |
| C/U Rich Region | Compounds | PolyU, PolyU, mRNA | | |
| Polyethylene Glycol (PEG) | Mers | 2000, 6000, 8000, 10000, etc. | 6000-8000 | |
| Dendrimer | Types | Tentical Chromatography media (higher product capacties when IMAC ligand is on a dendrimer linker) | | |
| Gels | Types | Polyacrylamide, Agarose, | | |
| Food Stuffs | Types | Single cell protein, removal of nucleic acids from food stuffs in general. | | |
| Digestion Enzymes | Types | DNASE, endo-nuclease, exo-nuclease | | |
| Products | Compounds | AIDS drugs comprising AZT, DDI, coenzyme A, acyclic purine nucleoside analogs (e.g. Acyclovir). | | |

[a]Chai, S. A., R. R. Beitle, and M. R. Coleman, "Facilitated Transport Metal Affinity Membranes," International Journal of Biochromatography, 2, 125-131, 1996.
[b]Oxford, C. A. Taylor, R. R. Beitle, and M. R. Coleman, "Effect of Chelated Metal on Amino Acid Transport in Faciliated Transport Membranes Incorporating Metal Affinity," ACS Symposium on Chemistry and Material Science of Synthetic Membranes, 1999.

DESCRIPTION OF THE DRAWINGS

The invention can be better understood with reference to the following detailed description together with the appended illustrative drawings in which like elements are numbered the same.

Figure 1:
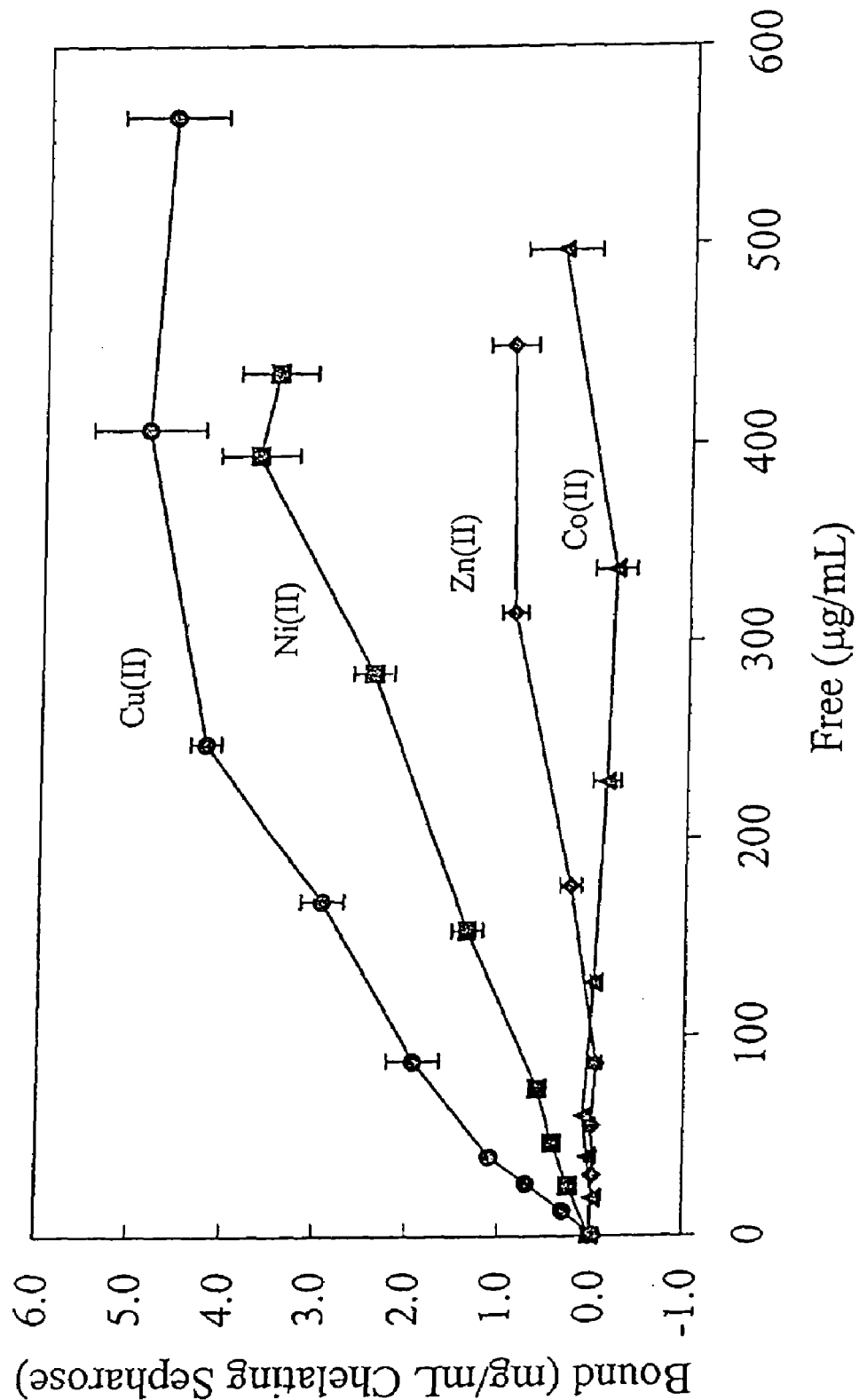
FIG. 1 graphs different isotherm binding curves for baker's yeast RNA interacting with different metal charged IDA Chelating Sepharose matrix in 10 mM HEPES with 250 mM NaCl at pH 7.0. The metal ions charged were Cu (II), Ni (II), Zn (II), and Co (II), to show the different affinities of each metal chelate toward bakers yeast RNA.

Table A gives preferred ranges for some of the parameters of the inventions

Definitions

The term "binding" to a IMAC ligand including an immobilized metal atom and/or ion means interacting with the metal atom and/or ion via any chemical and/or physical mechanisms including, without limitation, hydrogen bonding, coordinate bonding, apolar, ionic or covalent bonding, electrostatic interactions, ionic interactions, covalent interactions, mixture or combinations thereof.

The term "non-shielded" means that a purine and/or pyrimidine groups are sufficiently exposed to be able to bind to metal atoms and/or ions immobilized in a matrix, i.e., an IMAC matrix. For example, RNA, co-enzyme A, denatured DNA are all examples of molecules that contain non-shielded purine or pyrimidine moieties or groups. On the other hand, duplex DNA or RNA are examples of shielded molecules containing purine or pyrimidine moieties or groups. Thus, the term non-shielded means a purine or pyrimidine moiety or group sufficiently exposed to be able to bind to a metal and/or ion in an IMAC matrix or ligand.

The term "a purine" includes a single purine or a plurality of purines (one or more purines) with the upper limit bound only by the number of purines in the molecular components being analyzed, which can be between one and millions and millions.

The term "a pyrimidine" includes a single pyrimidine or a plurality of pyrimidines (one or more pyrimidines) with the upper limit bound only by the number of purines in the molecular components being analyzed which can be between one and millions and millions.

The term "or" includes "and/or" as well as simply or. Thus, purine or pyrimidine means purine and/or pyrimidine.

The term "IMAC matrix" means a molecular component including immobilized metal atoms and/or ions capable of binding non-shielded purines or pyrimidines. The matrix generally comprises a polymer having a ligand attached thereto, where the ligand is capable of immobilizing the metal atoms and/or ions.

The term "ligand" generally means a molecule having a site for binding a metal atom or ion. As used herein the ligands are generally chemically bonded to a substrate so that the binding site can extend into a medium. The ligand, free or bound to a substrate, is then brought in contact with a desired metal atom or ion or mixture of metal atoms and ions to form an immobilized metal atom or ion bearing (an IMAC) reagent. The IMAC reagent can then be used to interact with solutions containing mixtures of compounds containing shielded and non-shielded purines and/or pyrimidines to the purpose of separation, isolation, purification, quantitation, or the like.

The term "IMAC ligand" means a ligand immobilizing a metal atom, ion or mixture thereof, where the metal atom, ion or mixture thereof is capable of binding compounds including a non-shielded purine moiety, a non-shielded pyrimidine moiety or a mixture thereof.

The term "COT" is used to describe the kinetics of hybridization between two nucleic strands in solution and is defined by the product of [nucleic acid]×(time). Put simply, when the concentration of two complementary strands in a solution is high, then it takes a shorter time for hybridization to occur than it does when one or both of the strands are present at a low concentration.

DETAILED DESCRIPTION OF THE INVENTION

The inventors have found that a compound containing a non-shielded purine or pyrimidine moiety or group such as a single-stranded nucleic acid molecule, e.g., an oligonucleotide or an RNA molecule or a molecule including A, G, C, T or U, have affinity to an IMAC matrix; while a compound that does not contain a non-shielded purine or pyrimidine moiety or group or easily accessible aromatic nitrogen on a purine or pyrimidine moiety or group, such as double-stranded DNA, RNA, RNA/DNA complexes, has little or no affinity to the same IMAC matrix. Thus, the inventors have demonstrated that the affinity of immobilized metals toward nucleic acid bases allows the use of IMAC in the separation of double strained nucleic acid polymers from single stranded nucleic acid polymers, the purification of plasmid DNA, RNA, and/or the removal of nucleotides and primers from PCR reactions.

Although the present invention is primarily directed to nucleic acids (DNA and/or RNA), the present invention enjoys much broader application in the fields of biomolecule separation, purification, identification, quantitation, etc., where the target molecule includes a non-shielded purine and/or pyrimidine moieties or residue. Such biomolecules include, without limitation, AMP, ATP, GTP, CTP, NAD, Coenzyme A, Hypoxanthine, Xanthine, Orotic acid, Inosine, or any other biomolecule having a purine and/or pyrimidine moiety sufficiently exposed to permit binding to an IMAC reagent of this invention.

The inventors found that purine-containing, single-stranded nucleic acid molecules, such as oligonucleotides or unstructured RNA molecules, can be selectively bound by IMAC matrices. The inventors assume that the binding may be similar to the binding of histidine, which is known to bind to IMAC matrices. The inventors found that soft metals avoid nonspecific interactions with backbone phosphates. (14-16) The inventors have found that the high, specific affinity of chelated soft metals for nucleic acid bases allows the use of IMAC in the purification of plasmid DNA and RNA, in the removal of contaminants and primers from PCR reaction products, and in the detection of mismatches in DNA heteroduplexes.

The present invention broadly relates to an immobilized metal affinity chromatography (IMAC) column including an IMAC matrix including immobilized metal atoms and/or ions capable of binding compounds containing non-shielded purine and/or pyrimidine moieties or groups. The present invention also broadly relates to an immobilized metal affinity chromatography (IMAC) instruments including an immobilized metal affinity chromatography (IMAC) column or absorbent including a matrix having immobilized metal atoms or ions capable of binding compounds containing a non-shielded purine or pyrimidine moiety or group.

The present invention also broadly relates to a method for separating different compounds containing a non-shielded purine or pyrimidine moiety or group by passing a solution containing the different compounds through an immobilized metal affinity chromatography (IMAC) column including a matrix having immobilized metal atoms or ions capable of binding compounds containing a non-shielded purine or pyrimidine moiety or group and analyzing the effluent from the column as a function of time or over a given period of time.

The present invention also broadly relates to a method for purifying a solution containing a major compound containing a non-shielded purine or pyrimidine moiety or group and a minor compound containing a non-shielded purine or pyrimidine moiety or group by passing the solution through an immobilized metal affinity chromatography (IMAC) column including a matrix having immobilized metal atoms or ions capable of binding compounds containing a non-shielded purine or pyrimidine moiety or group and analyzing the effluent from the column as a function of time or over a given period of time. The column can include metal atoms or ions that have a higher or lower binding affinity for the major verses the minor compound and separation will results, provided that the binding affinities are indeed different.

The present invention also broadly relates to a method for purifying a solution containing a compound that does not contain a non-shielded purine or pyrimidine moiety or group and a compound that does contain a non-shielded purine or pyrimidine moiety or group by passing the solution through an immobilized metal affinity chromatography (IMAC) column or absorbent including a matrix having immobilized metal atoms or ions capable of binding compounds containing a non-shielded purine or pyrimidine moiety or group and analyzing the effluent from the column as a function of time or over a given period of time.

The present invention also provides a method for removing fluorophore tagged nucleotides or nucleosides from a solution involving passing the solution through an IMAC column capable of either binding to nitrogen atoms of a base residue in the nucleotides or nucleoside, binding to atoms and/or functional groups of the fluorophores or both and removing all non-bound materials from the column. Thus, fluorophore labeled nucleotides or oligonucleotides can be removed from the solution.

The present invention also provides a separation technique involving a compound column including an IMAC zone and another separation zone. Because the IMAC technique is relatively insensitive to the ionic strength of a solution, an IMAC zone can be used to bind compounds including non-shielded purine or pyrimidine moieties or groups such as RNA and other single stranded nucleic acids followed or preceded by a zone designed to affect a separation of the other constituents of the solution based on the other constituents interaction with the stationary material of the other constituents. Thus, an upper disk, region or zone of a column having a IMAC region will bind the compounds having a non-shielded purine or pyrimidine moiety or group pulling them out of solution before a second section, region or zone of column having a different stationary phase such as an anion exchange material or HIC material. This type of compound column can be made using monolith technology and running a small amount of IMAC ligand onto an activated column and then flooding the rest of the column with one or more additional ligands, quenchers or stationary phases.

The present invention also relates to IMAC pre-filters for purifying solution containing large quantities of plasmid.

Thus, a short column coated with an IMAC coating to the present invention is used to bind and remove RNA and other contaminants bindable by IMAC (e.g., on a sample loading loop) before performing more complete purification on large anion exchange columns, HIC, size exclusion or some other type of column.

The present invention also relates to a plasmid separation technique using membranes coated with or impregnated with an IMAC matrix which filter or prevent free RNA or molecules containing non-shielded purines or pyrimidines from migrating to the other side of the membrane structure.

The present invention also relates to a magnetic object such as a bead, stirring rod, or the like either coated with an IMAC ligand or where the object has a porous outer surface to which an IMAC ligand has been bonded to, deposited thereon or therein. The present invention also relates to the use of these magnetic objects to batch-wise purify samples containing target single stranded nucleic acid sequences such as RNAs, oligonucleotides, or the like where the single stranded nucleic acid sequences bind to the magnetic object, which can then be removed from the solution, washed free of contaminates and eluted to recover the single stranded nucleic acid sequences. Alternatively, the magnetic IMAC objects can be used to purify double stranded nucleic acid sequences by removing contaminating single stranded nucleic acid sequence, e.g., purifying plasmids or the like.

The present invention also relates to metal beads coated with a composition including an IMAC ligand to batch bind RNA, single stranded DNA, single stranded oligonucleotides or oligonucleosides or the like from a solution containing double stranded DNA such as plasmids to clarify the solution, where the bead can be separated from the solution via magnets.

The present invention also relates to an assay using IMAC matrices deposited in wells of microplates or included in a medium comprising the wells of the microplate and then binding a single stranded oligonucleotide having a fluorescent tag to the matrix. The IMAC matrix either contains a quencher in close proximity to the metal binding sites or uses the substrate upon which the IMAC is coated as a fluorescent quencher. When a complimentary sequence is added to a well containing the fluorescent tagged oligonucleotide, the two pair. The paired sequence is released and the tag fluoresces. This assay represents an inexpensive route to the construction of DNA chip analogs without all of the currently needed fancy lasers, scanners, and fluidics systems.

The present invention also relates to an assay using IMAC matrices deposited in wells of microplates or medium added to the wells of the microplate or medium added to the wells of the microplate and then binding a single-stranded oligonucleotide having a first tag to the matrix. The IMAC matrix either contains a second tag in close proximity to the metal binding sites or associated with the substrate upon which the IMAC is coated acts, where the tags interact to produce a fluorescent pair. When a complimentary sequence is added to a well containing the fluorescent tagged oligonucleotide, the two pair. The paired sequence is released and the fluorescence stops.

When using a matrix, the bound single-stranded fluorophore is physically obstructed from the light path. When a complementary sequence is added, the fluorophore goes into solution where it is exposed to light and fluoresces.

The present invention also relates to an assay using substrates coated with IMAC so that a separate fluorophore is placed in the wells to create a large stoke shift when the fluorescent tagged oligonucleotide is bound and a normal fluorescent stoke shift when the oligonucleotide is not bound to the IMAC ligand.

The present invention also provides a method for separating poly(A) tailed mRNA from eukaryotic cells including the step of passing a solution comprising eukaryotic cell mRNA through an IMAC column including an IMAC matrix or passing the solution over an IMAC matrix or contacting the solution with magnets coated IMAC particles and separating poly (A) tailed mRNA from other mRNA, where the poly(A) tailed mRNA elutes from the IMAC matrix last because the poly(A) tail has a higher affinity for IMAC matrix—the poly(A) tails are usually 50-200 bases long.

The present invention also relates to a method for separating denatured nucleic acid sequences having A rich regions from the complementary strand having T rich regions.

The present invention also relates to a method for separating denatured nucleic acid sequences having C rich regions from the complementary strand having G rich regions.

The present invention also relates to a method for separating denatured nucleic acid sequences having A-G or A-C rich regions from the complementary T-C or T-G rich regions.

The present invention also relates to IMAC ligand or matrices deposited on capillary walls or in solution (e.g., IMAC ligands or matrices bonded to, associated with or deposited on PEG or dendrimer), where the IMAC ligand or matrix would alter the retention times of compounds having non-shielded purine and/or pyrimidine moieties in capillary electrophoresis. The present invention also relates to IMAC ligand or matrices deposited on a surface or in a gel, where the IMAC ligand or matrix alters retention times of compounds having non-shielded purine and/or pyrimidine moieties in the gel or on the surface, e.g., slab gel electrophoresis. In each case, unhybridized single strands, or duplexes bearing mismatches, or duplexes bearing overhangs, or partially single-stranded molecules have longer retention times are retained more. This process can also be performed in an on-off fashion (bound, unbound in a single theoretical plate), e.g., in a microtiter well or on IMAC beads.

The present invention also relates to improving mass spectrometry analysis of complex nucleic acid mixtures by adding a composition including an IMAC compound or matrix capable of binging compounds having non-shielded purine or pyrimidine moieties or groups. After binding, the shielded molecules would have their normal mass to charge responses, but the molecules bindable to the IMAC ligand would have a mass to charge ratio based on the base molecule and number of IMAC ligands associated with the molecule. Additionally, if the IMAC MS fragmentation pattern is known, the bound materials fragmentation pattern can be easily extracted.

The present invention also relates to a fluorophore-bearing-IMAC-functionality molecule used for hybridization and/or mismatch detection using polarization or quenching/enhancement, also by retention, partitioning, precipitability, non-dialyzability.

Several of these applications will work best with temperature gradients or at elevated temperatures, or in the presence of denaturants or competitive elutants.

The present invention also relates to the use of IMAC ligands or matrices in the purification of cellular or viral RNA and non-natural RNA analogs, especially peptide nucleic acids and modified forms used as aptamers. The present inventions also relates of the use of IMAC in conjunction with many of the DNA applications of hydroxyapatite, e.g., COT curves for complexity of a DNA sample, or genome and for enriching sequences of interest by subtractive hybridization.

The present invention also relates to cell type recognition, differentiation and identification by separating duplexed nucleic acid sequences from non-duplexed sequences where one set of sequences comprises the mRNA of one cell type and the other set of sequences are complementary mRNA or cDNA derived from the mRNA of a second cell type. Thus, the mRNA form one cell type can be hybridized with the complementary mRNA or cDNA of the second cell type. The solution is then separated over an IMAC substrate where the IMAC substrate would bind non-paired mRNAs and/or mismatched paired molecules. The bound material can then be extracted from the IMAC substrate and tested to determine specific differences between the mRNAs of each cell line. This technique can be used to determine cite mutations in cancer versus non-cancer cell lines or wild-type versus mutant cell lines. Alternatively, the technique can be used to look for homologous sequences across species where nucleic acid sequences (mRNA, chopped DNA, or denatured DNA) from one species are mixed with complementary nucleic acid sequences of the same type from another species. Separating all hybridized or partially hybridized material from all single-stranded material and analyzing the hybridized material. Once separated, the nucleic acid sequence of interest can be increased enriched for cloning and/or sequencing, chelated-metal-based nucleic acid stains and dyes, e.g., for identification of dead (permeable) cells or unhybridized spots in arrays (still single-stranded)chelated-metal-based precipitants.

The present invention also relates to nucleic acid affinity precipitation using composition having two or more metal chelating agents binding metals capable of binding compounds having non-shielded purine or pyrimidine moieties or groups. Such compositions can be used to bulk precipitate RNA, single stranded DNA or other molecules having non-shielded purine or pyrimidine moieties or groups. The compositions can include those composition disclosed in U.S. Pat. Nos. 5,310,648 and 5,283,339, incorporated herein by reference. Additionally, the composition can be any soluble oligomeric or polymeric material that includes chelating groups capable of chelating metals with affinities for compounds having purine or pyrimidine moieties or groups.

Additionally, the backbone or spacer groups can be labile (designed to be chemically and/or physically removable) to such processes as a redox reaction (redox-cleavable) or photochemically labile to facilitate re-solubilization of the precipitated material. Moreover, functionalized dendrimers having metal chelating groups are acceptable compositions.

The present invention also related to IMAC chelating agents having multiple chelating agents so that multiple metals can be bound to the IMAC matrix. These multimetal IMAC matrices can be used to perform separations or assays based on IMAC affinity for nucleic acids in the presence of a competitive ligand, such as histidine, etc. to reduce non-specific binding.

The present invention also relates to denaturing IMAC chromatography of nucleic acid sequences using chemical gradient and/or temperature gradient and/or other denaturing environments so that the method would separate nucleic acid sequence based on their denaturing characteristic which would allow them to bind to the IMAC ligands in the stationary phase.

The present invention also relates to elution with adenosine, ATP, AMP, GTP or with elution in displacement-chromatography.

The present invention also relates to a method for purifying composition having a non-shielded purine or pyrimidine moiety or group from a crude mixture of materials. This method would be especially useful in the purification of AIDS drugs such as AZT, DDI or the like. The method would also be especially useful in the purification of ribavirin, riboflavin, acyclovir, inosine, s-adenosyl methionine or other natural products or pharmaceuticals that include a non-shielded purine or pyrimidine moiety or group.

The present invention can also be used to strip out nucleotide and/or nucleosides and/or nucleic acid sequences from lysates or other composition containing protein and nucleic acid sequences and monomers to derive food stuffs for animal including human consumption using IMAC ligands or matrices. In addition, the stripping step can be preceded by treating the lysates or other protein rich compositions with nucleases or ribonucleases to convert large nucleic acid sequence to smaller nucleic acid sequences or monomers. Once the nucleotide or nucleosides or nucleic acids have been recovered from the IMAC ligands or matrices, the nucleotide or nucleosides or nucleic acids can be separated and purified to provide a large scale source of nucleotide or nucleosides or nucleic acids.

The present invention also relates to a purification method for nucleic acids involving subjecting a mixture of nucleic acids of a DNase and separating the resulting fragments.

The present invention also relates to an IMAC column having a ½ Copper (II) ions or a similar ion that binds aromatic nitrogen, imidazol groups and ½ with an ion like Ti(III) or Cr(II) that prefers ketogroups. Using such mixed metal IMAC columns one can achieve higher affinity for contaminants (e.g., RNA in plasmid DNA) or improve selectivity.

The present invention relates to substrates having deposited thereon or therein IMAC ligands or derivatives IMAC ligands, where the derivatization allows the IMAC ligand to bond to reactive groups on the substrate surface or within the substrate.

The present invention also relates to methods of separating using an IMAC ligand containing solid material in a fluidized bed configuration, where a solution is force through the material in an upflow condition resulting in fluidization of the material and the material of interest binds to the material or the contaminants bind to the material. The material of interest or contaminant can then be released from the material using a displacement agent.

The present invention also relates to separating a library of single-stranded nucleic acid sequence having a poly A leader or trailer from their complimentary sequences where the sequences where derived from a plasmid which has undergone random mutations in a tissue culture.

An additional preferred embodiment of the IMAC device is the use of mixtures of metal ions to vary affinity for unshielded purines and pyrimidines. These mixtures could be used to vary affinity for specific sequences since certain metals have high affinity for purines and others have high affinity for pyrimidines. These mixtures could result in a superior device for many of the examples stated here-in.

The present invention also relates the separation of PNA (Peptide nucleic acids (PNA) are DNA mimics with a pseudopeptide backbone. PNA is an extremely good structural mimic of DNA (or RNA), and PNA oligomers are able to form very stable duplex structures with Watson-Crick complementary DNA, RNA (or PNA) oligomers, and they can also bind to targets in duplex DNA by helix invasion.) via a polypurine (or polypyrimidine tail) since PNA is not degradable by nucleases, a deoxyribose tail could be used as a tag that would bind an IMAC resin selectively with a high affinity. Then after separation the tail could be destroyed by nuclease digestion using DNAse immobilized to a solid support or just DNA. It would be fairly simple to separate the PNA from the bases left behind.

The present invention also relates to substrates including a concentration gradient of IMAC ligands bonded thereto, where the gradient extends for a profile of the substrate such as from a front edge of the substrate to a back edge of the substrate, with slices of the substrate at right angle to the gradient has a constant IMAC ligand concentration. The substrate can be a gel on a gel plate or a column substrate or any other substrate commonly used in gradient gel separations or other similar analytical separation techniques.

The present invention also relates to the use the gradient IMAC ligand substrates to separation and/or focus mixtures of nucleic acid sequences, compounds having a non-shielded purine, a non-shielded pyrimidine, or mixtures thereof, of the like.

The present invention also relates to imprinting on a surface an IMAC ligand or a substrate having an IMAC ligand bonded thereto for the construction of a patterned surface having IMAC ligand regions and IMAC ligand free regions. The substrate can be a chip and the IMAC ligand regions can be treated with a probe so that probe association with nucleic acid sequences including a complimentary probe subsequence can be directly identified by a change in the electrical properties of the circuit on the chip below an IMAC ligand region from which its probe has been release due to interaction with its complimentary subsequence.

The present invention also relates to the purification of oligonucleotides prepared using the Merrifield solid phase oligomerization technique.

The present invention also relates gradient HPLC methods for purifying complex mixtures of solutions containing compounds including a non-shielded purine, a non-shielded pyrimidine, or mixtures thereof and compounds including a shielded purine, a shielded pyrimidine, or mixtures thereof.

Suitable IMAC ligands for use in this invention include, without limitation, any molecule having a molecular moiety or group capable of coordinating or chelating a metal atom or ions. One preferred type of IMAC ligand comprise molecules having a linear or branched carbohydryl group (carbon-containing group) and a head group capable of binding a metal atom or ion having the formula Z-R, where Z is a group capable to binding a metal atom or ion and R is a linear or branched carbohydryl group having between about 1 and about 50 carbon atoms or more or $CH(R')CH_2[OCH(R')CH]_n$ where R' is H or methyl and n is chosen so that the compound has a molecular weight prior to metallation between about 1500 to about 20,000. Other preferred type of IMAC ligand comprises molecules including a head group, a linking group and a tail group represented by the formula Z-R-Z', where Z is a head group capable of immobilizing a metal atom or ion, R is as described above, and Z' is a tail group. The tail or Z' group can be the same of Z or a group designed to chemically bound to a substrate so that the head group, Z, is tethered from the substrate by the linking group R. Such substrate reactive Z' groups include, without limitation, OH, COOH, COOR", SH, or other groups capable or reacting with a substrate such as sepharose, agarose, polyacrylamide, or similar substrates, where R" is the same or different from R, but shares the same definition. Again, R can have from 1 to 50 carbon atoms or more. R can be an alkyl group, an alkenyl group, an alkynyl group, an aryl group, an alkaryl group, an aralkyl group, a group where one or more carbon atoms from been replaced by a hetero atom such as N, O, P, S, Si or the like. The head or Z groups can include, without limitation, (a) —$N(CH_2COOH)_2$; (b) —$NHCH_2CH_2NHCH_2CH_2NH_2$; (c) —$NHCH_2CH_2N(CH_2CH_2NH_2)_2$; (d) —$NHCH_2CH_2CH_2NHCH_2CH_2NHCH_2CH_2NH_2$; (e) —$NHCH_2CH_2NHCH_2CH_2NHCH_2CH_2NH_2$; (f) —NHCH (X)COOH (D- or L-amino acids); (g) —$N(CH_2COOH)CH(X)COOH$[D- or L-N-(carboxymethyl)amino acids], where X in f and g is H, $CH_3$, $CH(CH_3)_2$, $CH_2CH(CH_3)_2$, $CH(CH_3)CH_2CH_3$, $CH_2CH_2SCH_3$, $CH_2OH$, $CH(OH)CH_3$, $CH_2$ SH; $CH_2COOH$, $CH_2CONH_2$, $CH_2CH_2COOH$, $CH_2CH_2CONH_2$, $(CH_2)4NH_2$, $(CH_2)_3NHC(NH_2)_2$; (h) $NHC(O)CH_2N(CH_2COOH)CH_2CH_2N(CH_2COOH)_2$; (i) —$NHC(O)CH_2N(CH_2COOH)CH_2CH_2N(CH_2COOH)CH_2CH_2N(CH_2COOH)_2$; (j) —$N(CH_2COOH)CH_2CH_2N(CH_2COOH)_2$. (k) —$YNHCH_2CH_2N(CH_2CH_2NH_2)_2$; (l) —$YNHCH_2CH_2CH_2NHCH_2CH_2NHCH_2CH_2NH_2$; (m) —$YNHCH_2CH_2NHCH_2CH_2NHCH_2CH_2NH_2$; (n) —$YOCH_2CH_2N(CH_2COOH)CH_2CH_2N(CH_2COOH)_2$; (o) —$YOCH[CH_2N(CH_2COOH)_2]_2$ wherein Y in PEG- and PPG-based compounds is $NHC(O)CH_2$ $CH_2$ $C(O)$ and in other compounds it is $C(O)$ only. The ligands also include those ligands described in U.S. Pat. Nos: 5,310,648 and 5,283,339, incorporated herein by reference, and any soluble oligomeric or polymeric material that includes chelating groups capable of chelating metals atoms or their corresponding ions having an affinity for compounds having a non-shielded purine or pyrimidine moieties or groups, or mixtures or combination thereof.

Particularly preferred head groups include, without limitations, IDA, iminodiacetic acid, (—$N(CH_2COOH)_2$, NTA, nitrilotriacetic acid, (—$CH(COOH)N(CH_2COOH)_2$), or other amine-carboxylic acid chelating groups.

Suitable IMAC metal atoms or ions for use in this invention include, without limitation, any metal atom or its corresponding ions from the Periodic Table of Elements capable of binding to a compound containing a non-shielded purine or pyrimidine moiety or group. Preferred metal ions include, without limitation, $Cu^{2+}$, $Zn^{2+}$, $Ni^{2+}$, $Fe^{3+}$, $Fe^{2+}$, $Co^{2+}$, $Sc^{2+}$, $Ti^{2+}$, $V^{2+}$, $Cr^{2+}$, $Mn^{2+}$, $Ca^{2+}$, $Cd^{2+}$ or $Hg^{2+}$ or mixtures or combinations thereof. Particularly preferred metal ions include $Cu^{2+}$, $Zn^{2+}$, $Ni^{2+}$, $Fe^{2+}$, or $Co^{2+}$ or mixtures or combinations thereof. More particularly preferred metal ions include $Cu^{2+}$ or $Ni^{2+}$ or mixtures or combinations thereof. For metal ions, the preferred complexes for attaining the desired ion includes, without limitation, any metal salt that is soluble in the metal charging buffers having a counterion that does not adversely affect the IMAC ligand or the substrate to which the ligand is bound. Preferred metal salts include metal halides such as metal fluorides, metal chlorides, metal bromides, or metal iodides or mixture thereof, metal carboxylates, metal carbonates or bicarbonates, metal nitrates, metal phosphates, metal sulfates, metal oxychlorides, metal or similar metal complexes. Particularly preferred metal complexes are the metal chlorides.

Suitable substrate upon which the IMAC ligands can be bonded to, attached to or associated with include, without limitation, non-capillary columns, capillary columns, gels, chip surfaces, microplate surfaces, large pore zeolites, mordenites, fugucites or the like, porous foams, porous resin, polymer beads including macroreticular beads, surfaces of non-porous monolithic structures such as inorganic monolithic structures used in catalytic converts or polymeric structures such as epoxide resins including CIM monoliths made by BIA Separations of Ljubljana, Slovenia, or the like.

Suitable polymer substrates for IMAC ligand functionalization, include, without limitation, sepharose, chemically and/or physically modified sepharose, agarose, chemically and/or physically modified agarose, other polymeric sugars or chemically and/or physically modified versions thereof, cellulose, chemically and/or physically modified cellulose, polyolefins, chemically and/or physically modified polyolefins, polydienes, chemically and/or physically modified derivative polydienes, polyurethanes, chemically and/or physically modified polyurethanes, polypeptides, chemically and/or physically modified polypeptides, polyamides, chemically and/or physically modified polyimides, polyalkyleneoxides, chemically and/or physically modified polyalkyleneoxides such as polyethyleneglycols, chemically and/or physically modified polyethyleneglycols, silicones, elastomers, thermoplastics, thermoplastic elastomers, or any other polymeric substrate.

Suitable membranes include, without limitation, impermeable membranes, permeable membranes or semi-permeable membranes or chemically or physically modified membranes.

Suitable inorganic supports include, without limitation, silicas, silicates, aluminas, silca-aluminas, zeolites, mordenties, fugasites, aluminates, clays, monoliths, honeycombed monoliths, or any other inorganic support or chemically or physically modified supports.

Suitable metallic supports include, without limitation, any metal such as gold, gold alloys, platinum, platinum alloys, silver, silver alloys, iron, iron alloys such any steel, copper, copper alloys such as brass or bronze, tin and tin alloys, aluminum and aluminum alloys, silicon and silicon alloys, other semiconductors, or the like or chemically or physically modified metallic supports.

Suitable electronic chip include, without limitation, any electronic devices having a surface capable of being chemically functionalized.

Suitable chemical and physical modification processes includes, without limitation, chemical functionalization with reactive chemical agents, ion and/or atom bombardment and/or implantation, reactive extrusion, chemical etching, chemical deposition, or any other chemical or physical modification that permits IMAC ligands to be bounded to a substrate.

DETAILED DESCRIPTION OF EXPERIMENTS OF THIS INVENTION

Protocols for Nucleic Acid Separation

Spin Column Separation Technique

One preferred method for practicing this invention is the so-called Spin Column Separation technique. This technique is useful for PCR product separation using nickel charged columns and possibly for plasmid mini-preps using copper charged columns. The techniques uses the following materials: (o) Chelating Sepharose Fast Flow, Amersham Pharmacia Biotech; (p) Snap on spin columns for microcentrifuge tubes from Promega; (q) Imidazol; (r) Ammonium Chloride; (s) Sodium Chloride; (t) HEPES; and (u) a metal ion source such as $CuCl_2$, $NiCl_2$, and $ZnCl_2$.

Spin Columns Preparation

This section describes the general procedure for preparing spin columns for subsequent use.

Promega mini-prep microfuge snap-on columns with Chelating Sepharose media from Pharmacia biotech were used. Load media in 70% EtOH was directed onto the minicolumns. Generally, 50 uL of load media was used per column; however, the amount of load medium can be reduced based on amount of nucleic acid in samples. The columns were then spun for ~1 minute at maximum speed in a microcentrifuge. Two 150 uL volumes of water were used to wash the columns. Two 150 uL volumes of a solution of 50 mM $X^{+2}Cl_2^{-1}$ in DI water was used to metallate the columns. The metallated columns were then washed with two 150 uL volumes of IMAC running buffer (250 mM NaCl, 20 mM HEPES at pH 7.0). At this point, the column are charged and ready to bind nucleic acids. The columns are then switched to clean microcentrifuge tubes for subsequent use.

Spin Column Binding

This section describes the general procedure for binding materials of interest to spin columns prepared as described above.

For lysate samples, the lysate is resuspended in IMAC running buffer and loaded directly onto the IMAC spin column. The column is then spun for about 1 minute at maximum speed in a microcentrifuge. For samples from DNA and/or RNA sequencer or PCR reactions or other sequencing protocols, the sample or reaction product is loaded directly onto a metal charged spin column, preferably a nickel charged spin column and centrifuge. The primers and bases bind to the spin column and the purified sequencing product passes through the column and can be recovered from the supernatant in the microfuge tube. For plasmid purification, the sample is loaded directly on to a metal charged spin column, preferably a copper charged spin column and centrifuge. In the case of plasmid DNA, the RNA and other contaminants bind to the spin column and the clarified plasmid can be recovered from the supernatant in the microfuge tube. The spin columns can then be eluted with EDTA and recharged or reuse.

Spin Column Elution

This section describes the general procedure used to elute a used spin column for recharging and reuse.

Generally, elution is accomplished by added 150 μL of an elution buffer to the spin column in the microfuge tube and centrifuging the column for ~1 minute at maximum speed on an Eppendorf microcentrifuge. There are several elutants that can be used including, without limitation; imidazole, ammonium chloride, histidine, etc. The choice of elutant will generally depend on the type of IMAC separation that was used. The elutant should be compatible with IMAC separations. The overall preferred elutant is imidazole. The elutant buffer generally is a 200 mM imidazole IMAC running buffer. The elution results in a pH shift from a pH 7 for the running buffer to a pH 3.5 for the elution buffer. An EDTA solution can also be used to strip the metal ions from the matrix.

The choice of metal used to charge the spin columns depends on the application. Generally, $Cu^{2+}$ charged spin column have the highest loading capacity, but is known to strongly bind even one exposed histidine in proteins. The inventors have confirmed that $Cu^{2+}$ also strongly binds biomolecules having even a single non-shielded purine or pyrimidine moiety. Thus, $Cu^{2+}$ may not be the metal of choice in separation applications—shows reduced discrimination between different molecules, but may be the metal of choice in purification applications designed to remove either double stranded nucleic acid sequences from single stranded impurities or vis-a-versa. On the other hand, $Ni^{2+}$ and $Zn^{2+}$ show modest binding capacities, but are known to bind proteins with two or more adjacent exposed histidines. Thus, $Ni^{2+}$ and $Zn^{2+}$ may represent the metals of choice in separation applications—show increased discrimination between different molecules, but may be less desirably in purification applications.

In this invention, spin columns were loaded with $Cu^{2+}$, $Ni^{2+}$ and $Zn^{2+}$ capacities of 6, 4, and 1 mg/mL matrix, respectively. There are relationships between selectivity and loading capacity that appear to affect separation and binding efficiencies as described more fully herein and are apparent from the data and allow for the formulation of separation protocols and methods for different systems.

Batch Binding

Another preferred method for practicing this invention is the so-called Batch Binding technique described below.

Media Preparation

Chelating Sepharose Fast Flow adsorbent (Amersham Pharmacia Biotech) was charged before isotherms were run. The Sepharose Matrix was pippeted into a 2.2 mL microcentrifuge tube and centrifuged at maximum speed in an Eppendorf microcentrifuge. After centrifugation, the supernatant was removed by decantation. Next, 0.5 mL of distilled water was added, vortexed, and decanted. This buffer wash was repeated 3 times. Next, 1 mL of a 50 mM solution of $CuCl_2$, $CoCl_2$, $ZnCl_2$, or $NiCl_2$ was added to the tube, vortexed, centrifuged, and decanted. This charging step was repeated 3 times to insure complete loading of the matrix. Next, the charged media was washed with IMAC binding buffer (20 mM HEPES containing 250 mM NaCl at pH 7.0), this wash was repeated twice. Finally, ½ of the matrix volume of IMAC buffer was added to the tube to make a slurry.

Binding

Binding is performed by adding slurried IMAC matrix, as prepared above, directly to a sample in an appropriate buffer. Although any buffer can be used, preferred appropriate buffers include any buffer that does not cause precipitates to form or cause lose of metal ions bound to the IMAC matrix. Therefore, the buffer preferably should not contain EDTA or a similar soluble metal chelating agent. The sample to which the slurried IMAC matrices can be added include, without limitation, PCR products, Sanger Sequencing reaction products, cell lysates, impure plasmid products, impure pharmaceuticals, impure RNA products, impure RNA-enzymes, or any other product including impurities having paired purines and/or pyrimidines or impurities having non-shielded purine and/or pyrimidines. The sample to which the slurried IMAC matrix has been added, can then be agitated if necessary and centrifuged after a sufficient time for binding.

Elution

Once binding is completed, elution can be performed in a manner similar to the elution step described in the spin column elution section above. The elution buffer can be chosen to fit the needs of the separation. Generally, to elute, the elution buffer is added to the recovered IMAC matrix from the binding section above. The solution can then be agitated or vortexed and centrifuged and the supernatant removed by decantation. The process can be repeated several time to ensure complete elution.

Plasmid DNA Separations Using IMAC

Another preferred method for practicing this invention is in the purification of plasmid DNA. This method generally entails the use of the following additional materials: (1) an FPLC System or similar fast flow preparative liquid chromatography system and (2) an HPLC column, where the column is either prepacked or packed before use with a substrate having IMAC ligands attached thereto such as a chelating Sepharose substrate, a chelating agarose substrate, a chelating polyacrylamide substrate, or other similar substrates modified with an IMAC ligand.

Plasmid Lysate Clarification:

Plasmid lysates were clarified by column chromatography using an FPLC system, such as FPLC systems available from Amersham Pharmacia Biotech. Two, 1 mL HyTrap chelating columns connected in series were used to separate/purify a sample containing pCMV Sport b gal plasmid DNA (Gibco BRL, 7.9 kb) and cell lysate impurities. The plasmid samples were prepared by solution-phase compaction precipitation as described in Murphy, et. Al., Nature Biotech., August 1999, incorporated herein by reference.

The HyTrap columns were first equilibrated with 10 column volumes of deionized $H_2O$, followed by a 50 mM $M^{2+}Cl_2$ solution, where $M^{2+}$ is a metal ion, preferably, $Cu^{2+}$, $Zn^{2+}$, $Ni^{2+}$, $Fe^{3+}$, $Fe^{2+}$, $Co^{2+}$, $Ca^{2+}$, $Cd^{2+}$ or $Hg^{2+}$ or mixtures or combinations thereof. The inventor found that the preferred metal ion for plasmid lysate clarification was $Cu^{2+}$. The $Cu^{2+}$ solution was continuously applied to the column until complete saturation was observed by 254 nm ABS measurement. Next, the columns were washed with 2 volumes of deionized water followed by equilibration with 10 column volumes of 10 mM HEPES, 250 mM NaCl, which is the preferred column running buffer. Plasmid samples were loaded directly onto the column. The column effluent containing the purified plasmid DNA was collected in plastic fraction tubes. After separation, columns were regenerated by first running 10 mM EDTA over the column, then a solution of 1 N NaOH and then 3 M NaCl.

The plasmid samples used in these examples were prepared using the solution-phase compaction precipitation method, which produces a lysate having >95% plasmid DNA and relatively low endotoxin levels. However, the present method of plasmid DNA purification can be used for any impure plasmid sample regardless of its manner of preparation.

RNA Separation Using IMAC

Another preferred method of this invention is the separation/purification of RNA. This technique also generally entails the use of the following additional materials: (1) an FPLC System or similar fast flow preparative liquid chromatography system and (2) an HPLC column, where the column is either prepacked or packed before use with a substrate having IMAC ligands attached thereto such as a chelating Sepharose substrate, a chelating agarose substrate, a chelating polyacrylamide substrate, or other similar substrates modified with an IMAC ligand. Preferably, HyTrap Chelating Sepharose columns from Pharmacia or Amicon columns packed with Chelating Sepharose Flow having an aspect ratio of 10 are used for RNA separation/purification.

RNA Separation

RNA was purified by column chromatography using an FPLC system such as the FPLC systems available from Amersham Pharmacia Biotech. Two, 1 mL HyTrap chelating columns connected in series were used to separate/purify samples including a b ribozyme, an *E. coli* expressed ribozyme having 83 bases, and cell lysate impurities.

The HyTrap columns were first equilibrated with 10 column volumes of deionized $H_2O$, followed by a 50 mM $M^{2+}Cl_2$ solution, where $M^{2+}$ is a metal ion, preferably, $Cu^{2+}$, $Zn^{2+}$, $Ni^{2+}$, $Fe^{3+}$, $Fe^{2+}$, $Co^{2+}$, $Ca^{2+}$, $Cd^{2+}$ or $Hg^{2+}$ or mixtures or combinations thereof. As with plasmid samples, the inventors found that the preferred metal ion for RNA lysate clarification was also $Cu^{2+}$. The $Cu^{2+}$ solution was continuously applied to the columns until complete saturation was observed—appearance of metal ions in the column effluent as measured using ABS measurement as 254 nm. The columns were washed with 2 volumes of deionized water and equilibrated with 10 column volumes of 10 mM HEPES, 250 mM NaCl, the preferred column running buffer.

Next, an RNA sample was loaded onto the column. Separation/purification was achieved by running a buffer gradient, where the gradient was column running buffer with 0 to 2 M $NH_4Cl$ therein. The ribozyme was eluted over this range of the $NH_4Cl$ gradient and collected in plastic fraction tubes.

After separation, columns were regenerated by first running 10 mM EDTA over the column, then a solution of 1 N NaOH and then 3 M NaCl.

The present invention is also applicable to the separation, purification and/or isolation of other types of RNA such as tRNA, mRNA, ribosomal RNA, other RNA containing enzymes, co-factors containing purine and/or pyrimidine moieties, co-enzymes containing purine and/or pyrimidine moieties, any bio or synthetic molecule containing an unshielded U, T, G, C or A, or the like.

Other Applications of IMAC with Nucleic Acids:

The present invention is also well-suited for use in single nucleotide polymorphism (SNP) detection. A preferred method of this invention involves using an HPLC IMAC column to detected SNPs, where this preferred methods has the advantage of exposing the SNP containing sample to a sufficiently large, preferably, maximum, number of theoretical separation plates, yet maintaining an acceptable separation speed. Other applications for which the present invention is ideally suited include, without limitation, the purification of RT PCR reactions, purification, separation or identification of DNA sequencing reaction products, separation of labeled oligonucleotides, separation of mixture of oligonucleotides, or the like.

In addition, the metal ion chelating ligands (IMAC ligands) such as the IDA ligand, the preferred ligand in Chelating Sepharose and most other IMAC media, has been derivatized and attached to other substrates including polyacrylamide, derivatized polyacrylamide, agarose, derivatized agarose or other substrates. These other substrates to which an IMAC ligand is attached, allow the IMAC method of this invention to be extended to electrophoretic and membranes separation techniques. These alternate metal immobilized substrates are also useful for nucleic separation providing interesting analytical possibilities for derivatized polyacrylamide gels (SNPs, etc.) and faster nucleic acid separations using columns or membranes. Thus, the IMAC analytical techniques of this invention are adaptable to running IMAC modified SNP HPLC columns to separate nucleotides and other nucleic acid containing molecules. The techniques are even applicable to attaining sequence information based on the observed differential IMAC matrix binding affinities of the different bases: A>G>C≧T.

Materials and Methods

Nucleic Acids Utilized

Plasmids used were pBGS19luxwt (Genbank #, 6 kb) and pCMVsportbgal (Gibco BRL, 7.9 kb). Total bakers yeast RNA (Sigma) was used for RNA binding studies. 20-mer oligodeoxynucleotides homopolymers were obtained from MWG Scientific. In addition, an *E. coli*-expressed ribozyme (86 bases) (18) was used in RNA binding experiments as a target molecule.

Batch Equilibrium Isotherms 1

Equilibrium adsorption isotherms were measured, in duplicate, in 1.9 mL microcentrifuge tubes (Fisher Scientific). Chelating Sepharose Fast Flow adsorbent (Amersham Pharmacia Biotech) was charged before isotherms were run. Matrix was pippeted into a 2.2 mL microcentrifuge tube, centrifuged at maximum speed in an Eppendorf microcentrifuge, and the supernatant was then decanted. Next, 0.5 mL of distilled water was added, vortexed, decanted as listed above, and then repeated twice. Then, 1 mL of 50 mM metal ion solution (either $CuCl_2$, $CoCl_2$, $ZnCl_2$, or $NiCl_2$) was added to the tube, vortexed, centrifuged, decanted, and then repeated twice to ensure complete loading of the matrix. Next, the charged media was washed with IMAC binding buffer (20 mM HEPES with 250 mM NaCl at pH 7.0) and repeated twice. The final step was to add a ½ volume of IMAC binding buffer to create a slurry.

In tube preparation for isotherm measurement, the following order of addition was followed: 20 mM HEPES (Sigma) pH 7.0 with 250 mM NaCl, nucleic acid dissolved in IMAC binding buffer, and 20 ml 50% by volume Chelating Sepharose adsorbent in IMAC binding buffer.

After vortexing, tubes were rotated end-over-end in a Roto-Torque Heavy Duty Rotator (Cole-Palmer Instrument Co.) for 10 minutes. After equilibration, the tubes were centrifuged in an Eppendorf microcentrifuge for 2 minutes and the supernatant was removed for nucleic acid concentration measurement by absorbance at 260 nm.

Batch Equilibrium Isotherms 2

Equilibrium adsorption isotherms were measured, in duplicate, in microcentrifuge tubes (Fisher Scientific). Chelating Sepharose Fast Flow adsorbent (Amersham Pharmacia Biotech) was charged with metal as follows: Chelating Sepharose was pippeted into a 1.9 mL microcentrifuge tube, repeatedly washed by the addition of distilled water, centrifuged and decanted. The matrix was loaded by 3 cycles of addition of 1 mL of 50 mM metal chloride solution, then vortexing, centrifugation, and decantation. Next, the charged adsorbent was washed three times with IMAC binding buffer (20 mM HEPES (Sigma) with 250 mM NaCl at pH 7.0). The final step was to add one volume of IMAC binding buffer to create a slurry.

For isotherm measurement the following order of addition was followed: IMAC binding buffer, nucleic acid dissolved in IMAC binding buffer, and 20 ml 50% by volume adsorbent in IMAC binding buffer.

After vortexing, tubes were rotated end-over-end in a Roto-Torque Heavy Duty Rotator (Cole-Palmer) for 10 minutes, a time found sufficient for equilibration in control experiments. After equilibration, the tubes were centrifuged in an Eppendorf microcentrifuge for 2 minutes and the supernatant was removed for nucleic acid concentration measurement by absorbance at 260 nm.

Homopolymer Isotherms 1

The oligonucleotides used were 20-mer homopolymers of A, G, T, and C. Isotherms were performed as detailed above except the total volume was 200 mL and the tubes were eluted with 385 mL of 500 mM imidazol in IMAC binding buffer (15 mL of the supernatant was left in solution). In addition, 4 mL of Chelating Sepharose Fast Flow was used charged with Ni (II) to perform these isotherms.

Homopolymer Isotherms 2

Homopolymer isotherms were measured as detailed above except in 0.6 mL microcentrifuge tubes with a total volume of 200 ml, containing 4 ml of Chelating Sepharose Fast Flow. The tubes were eluted with 385 ml of 500 mM imidazole in IMAC binding buffer (15 ml of the original supernatant was left in solution making the actual volume 400 ml).

Plasmid Lysate Clarification 1

Plasmid lysates were clarified by column chromatography using an FPLC system (Amersham Pharmacia Biotech). A 20 mL Amicon FPLC column (1 cm×15 cm bed height) was used along with pCMVsportbgal plasmid DNA containing cell alkaline cell lysates. Columns were first equilibrated with 10 column volumes of DI $H_2O$. Next, 50 mM metal ion solution (chloride salt) was applied to the columns until complete saturation was observed. Then, the column was washed with 2 volumes of water and then equilibrated in IMAC binding buffer with 10 column volumes. Plasmid samples were loaded directly onto the column. After separation, columns were regenerated by first running 10 mM EDTA over the column, then a solution of 1 N NaOH and 3 M NaCl.

Plasmid Lysate Clarification 2

Plasmid lysates were clarified by column chromatography using an FPLC system (Amersham Pharmacia Biotech) and a 20 mL Amicon FPLC column (1 cm×15 cm). Columns were first equilibrated with 10 column volumes of deionized water, and 50 mM metal chloride solution as applied to the column until complete saturation was observed by monitoring absorbance at 254 nm. The column was then washed with 2 volumes of water and equilibrated in IMAC binding buffer over 10 column volumes. Plasmid samples were loaded directly onto the column. After separation, columns were regenerated with 50 mM EDTA at pH 8.0 and then a solution of 1 M NaCl in 1 N NaOH.

PCR Reaction Cleanup 1

PCR reactions were run on a Perkin-Elmer GeneAmp 2400 PCR system using (for a 100 mL reaction) 3 units of Promega Taq polymerase, 10 mL Promega 10× reaction buffer with $MgCl_2$, and Promega total dNTPs. The selected target was a 7 Kb plasmid 0.25 mg/100 mL reaction pCMV sport b gal (Gibco) with the forward and reverse PCR primers (1 mM of each primer/100 mL reaction) SEQ. ID NO. 1 5' TAATTGT-TGCCGGGAAGCTAGAG 3' and SEQ. ID NO. 2 5' TCG-CATTGAATTATGTGCTGTGTAG 3'(MWG Biotech), which amplified an 800 base region of the plasmid DNA. The PCR was run for 25 cycles at the following temperatures: Denaturing at 94° C. (5.5 min), primer annealing at 55° C. (0.5 min), and base extension at 72° C. (7.5 min).

Promega mini-prep microfuge snap on columns with Chelating Sepharose media from Pharmacia biotech were used to make spin columns and on each snap on column 100 mL of media (in 70% EtOH) was loaded directly onto the mini-column Then columns were centrifuged for ~1 minute at max speed in an Eppendorf microcentrifuge. Next, water (150 mL), metal ion solution (50 mM metal ion X (II) in DI water, 150 mL), and wash with IMAC running buffer (250 mM NaCl, 20 mM HEPES at pH 7.0, 150 mL) was run over the column twice. At this point, the column was charged and ready to bind nucleic acids. The columns were then switched to clean microcentrifuge tubes and the PCR reaction was loaded directly onto the column.

PCR Reaction Cleanup 1

PCR reactions (100 mL) were run on a Perkin-Elmer Gene-Amp 2400 PCR system using 2 units of Taq polymerase, 10 mL of 10× reaction buffer with MgCl2, and 800 mM dNTPs (all from Promega). The target was 40 pg/reaction of pCMV sport b gal (Gibco) with the forward and reverse PCR primers (0.1 nmol each) SEQ. ID NO. 3 5' TAA TTG TTG CCG GGA AGC TAG AG 3' and SEQ. ID NO. 4 5' TCG CAT TGA ATT ATG TGC TGT GTA G 3' (MWG Biotech), which amplified an 800 base region of the plasmid DNA encoding beta-lactamase. The PCR was run for 25 cycles of denaturation at 94 ffC (45 seconds), annealing at 55 ffC (30 seconds), and extension at 72 ffC (3 minutes).

Promega mini-prep microfuge snap-on columns filled with 100 mL Chelating Sepharose were used as spin columns. The columns were washed with water, charged with metal chloride solution (50 mM metal chloride in DI water), and finally washed with IMAC running buffer. The columns were then switched to clean microcentrifuge tubes and the PCR reactions were applied directly onto the spin columns.

Mismatch Detection

Duplexes of oligodeoxynucleotides with internal, single-base mismatches were all based on the same 50% G/C 20-mer oligonucleotide SEQ. ID NO. 5 (5' CAG ACG ATA GTC CTA GTT GC 3') and its complement. Mismatch detection used a 7 mm×7 cm Toso Haas HPLC chelating column run at 1 mL/min on a Waters 600E HPLC system.

Oligonucleotides were resuspended in IMAC running buffer, allowed to hybridize at 42 ffC for 10 minutes, and loaded via a 400 mL loop. Elution was by four column volumes of IMAC running buffer and a gradient from 0 to 14 mM imidazole in IMAC running buffer. The column was regenerated by 10 mM EDTA followed by a solution of 3 M NaCl in 0.1 N NaOH.

EXAMPLES

Equilibrium Adsorption Isotherms 1

To test binding capacities and trends, equilibrium adsorption isotherms were run to find affinities of RNA and DNA to IMAC matrices. The first experiment ran was to distinguish the different binding affinities of RNA and double-stranded DNA. In the example, equilibrium isotherms were performed using Zn (II) charged IDA IMAC resin using total bakers yeast RNA and pBGS19Luxwt plasmid DNA. The resulting isotherms showed no apparent binding of the plasmid DNA, but a defined binding isotherm for bakers yeast RNA. This experiment represented was the first evidence of differential binding affinity to an IMAC reagent for single-stranded RNA and double-stranded DNA.

Next, binding isotherms were run using different divalent metal ions ($Cu^{2+}$, $Ni^{2+}$, $Zn^{2+}$ and $Co^{2+}$) and total bakers yeast RNA to determine the relative binding efficiencies. FIG. 1 shows the isotherms for each divalent metal ion. From the isotherms is it apparent that each metal has a unique isotherm plateau, i.e., the plateau for each metal ion occurs at a distinct value of bound material. This plateau value corresponds to the loading capacity of the matrix. The RNA binding efficiencies for each metal For copper, nickel, zinc, and cobalt charged IMAC matrix are 5, 3.5, 1 and 0 mgs, respectively. RNA capacity of Cu (II) charged IDA-Sepharose was confirmed by breakthrough curve analysis (not shown). The trends in these isotherms do not follow the metal ion's positions on the periodic chart, but do follow the known trends seen for protein binding behavior to IMAC matrices. Cu (II) is known to bind a single exposed histidine residue; Zn (II) and Ni (II) bind at a minimum of 2 adjacent exposed histidine residues; and, Co (II) is even more selective for a 6 his tag.

The different metals have different affinities for nucleic acids. Each metal has a different trade-off between loading capacity and selectivity. Cu (II) has a higher affinity for nucleic acids, while Ni (II) has a higher selectivity for nucleic acid components. For applications where a very high binding affinity is desired (plasmid separation, etc.), Cu (II) is the metal of choice. However, if gradients are run to get a specific product from a mixture (RNA separations, PCR product cleanup), selectivity is more important and Ni (II) and/or Zn (II) should be considered.

Equilibrium Adsorption Isotherms 2

Preliminary experiments using Zn(II)-charged IDA-Sepharose with total bakers yeast RNA and pBGS19luxwt plasmid DNA showed considerable binding of RNA, but no apparent binding of the plasmid DNA.

Figure 2:
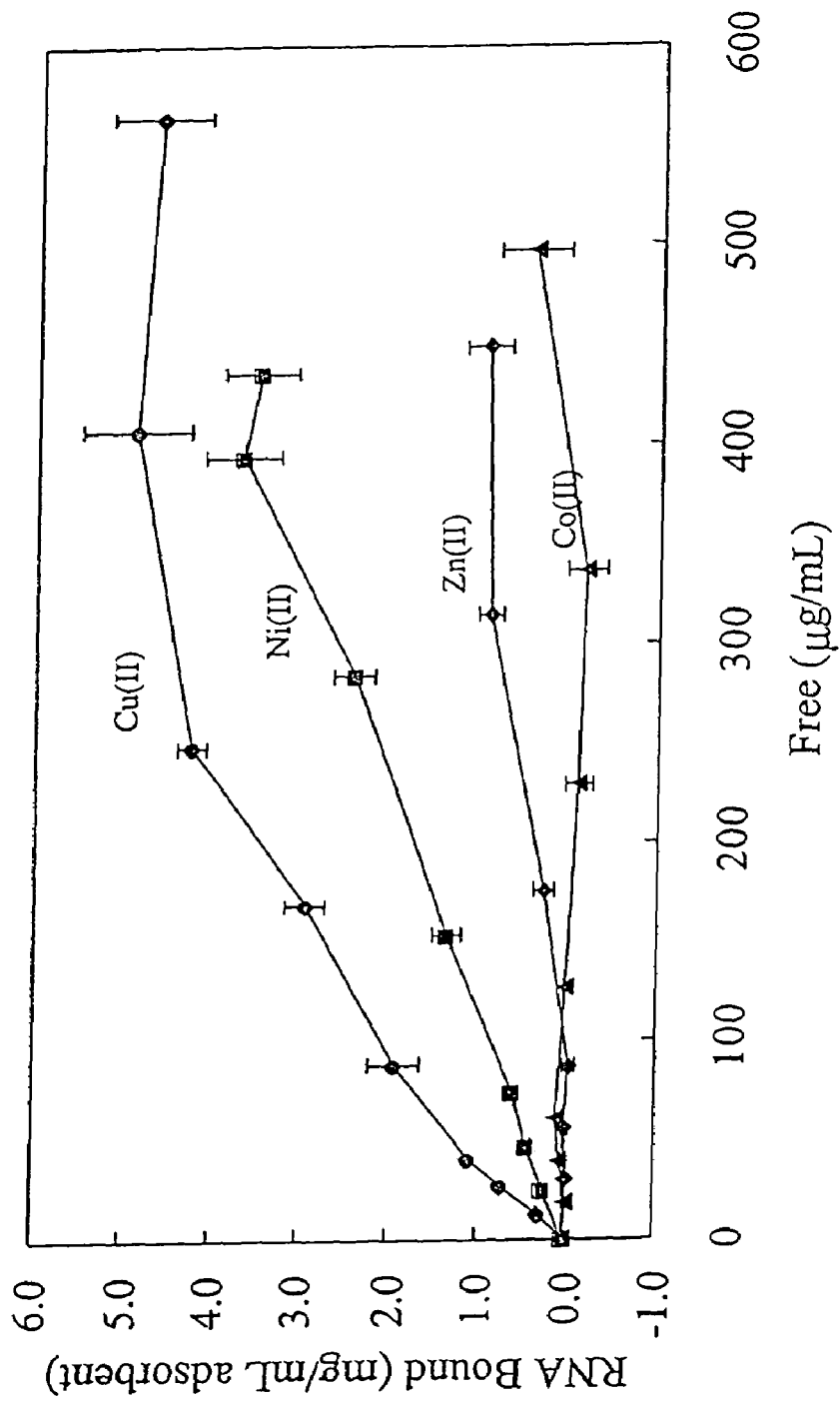
FIG. 2 graphs equilibrium adsorption isotherms for bakers yeast RNA on Chelating Sepharose charged with various metals with 250 mM NaCl in 20 mM HEPES at pH 7.0.

The adsorption of RNA on IDA-Sepharose loaded with various metal ions is illustrated in FIG. 2. The amount of RNA bound per mL of IMAC matrix for copper, nickel, zinc, and cobalt are 5, 3.5, 1 and 0 mg, respectively. The dynamic RNA capacity of Cu(II)-charged IDA-Sepharose was found by breakthrough curve analysis (at ~100 cm/hr flow rate) to be 5-7 mg/mL (not shown). The metals' RNA affinities follow the established trend of IMAC protein binding behavior.

Binding of 20-mer DNA Homopolymers 1

Figure 3:
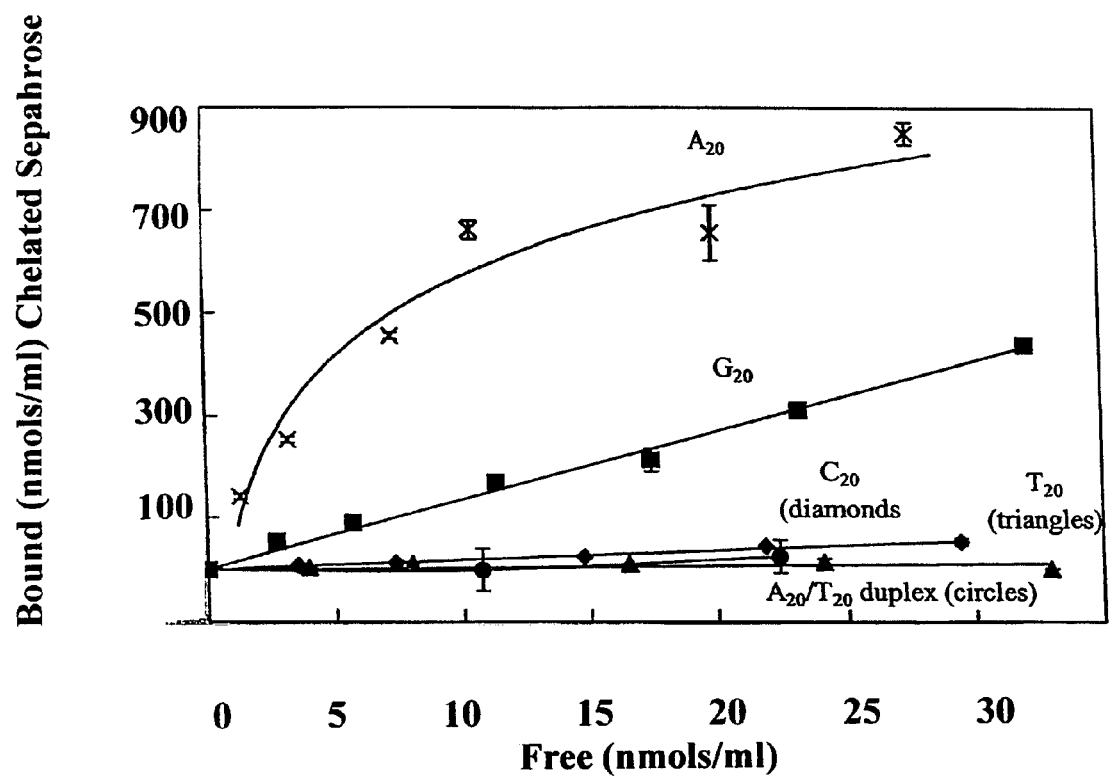
FIG. 3 graphs isotherms of 20-mer homopolymer oligonucleotides showing the different affinities of each base (A, G, C, and T) toward a Ni (II) charged IDA Chelating Sepharose matrix in 10 mM HEPES with 250 mM NaCl at pH 7.0.

To further explore the mechanism by which IMAC matrices bind nucleic acids, oligonucleotides were obtained, which were 20-mer homopolymers of A, G, T, and C on a deoxyribonucleic acid backbone. Isotherms were performed using Ni (II) charged IMAC resin and the resulting curves are shown in FIG. 3. Poly (A) bound with the highest affinity, while poly (G) had an approximately 10 times binding efficiency or selectivity. Poly (C) had a slightly higher affinity for IMAC matrix than that of poly (T). In addition, duplexes of the A and T homopolymers and duplexes of th G and C homopolymers had no binding affinity to the IMAC matrix charged with Ni (II).

Langmuir fits were performed on these homopolymer isotherms and $q_{max}/K_d$ was plotted. The $q_{max}/K_d$ of poly (A) is approximately 10 times higher than that of poly (G) and the $q_{max}/K_d$ of poly (C) is roughly 5 times higher than that of poly (T). Generally, these trends are thought to result form the structure of the nucleic acid bases. Adenine lacks a hydrogen atom at the nitrogen atom at position 1 and has a ½ character aromaticity through resonance. Guanine has an amine at position 2 compared to a hydrogen atom in the case of adenine, potentially adding an additional steric hindrance to the binding of metal ions to the position 2 nitrogen. A similar structural difference is seen in the purines where thymine has a hydrogen atom at position 3 that could lower the affinity of thymine compared to cytosine.

These isotherms lead to some guideline when using IMAC matrices to bind nucleic acids. First, the IMAC charged matrix does not appear to bind the phosphate backbone or the sugar moieties of the nucleic acid oligomers or polymers. The low affinity of Ni (II) charged IMAC resin toward poly (T) homo-polymer is clear evidence that the binding is not purely a backbone effect, since poly (A) and poly (G) showed relatively large binding affinities for the IMAC matrix. Moreover, because duplexed nucleic acid oligomers or polymers did not bind to the IMAC matrix, the binding does not occur at either the phosphate backbone structure or the sugar moieties. Furthermore, because single-stranded oligonucleotides bind to the IMAC matrix, but the duplexes of the A/T and G/C homopolymers do not, the interaction appears to be based on affinity of the IMAC matrix toward the actual exposed bases on the single-stranded nucleic acids (or single stranded regions of larger nucleic acid molecules).

Second, the separation appears to be dependent on the number of single stranded purines available for interaction with the IMAC matrix. With the purines having such a large binding capacity, the method can be used to differentiate nucleic acid sequence with different purine to pyrimidine contents, especially at the extremes of purine and pyrimidine content. Thus, the higher the single-stranded purine content, the higher the affinity for the IMAC matrix.

Binding of 20-mer DNA Homopolymers 2

Figure 4:
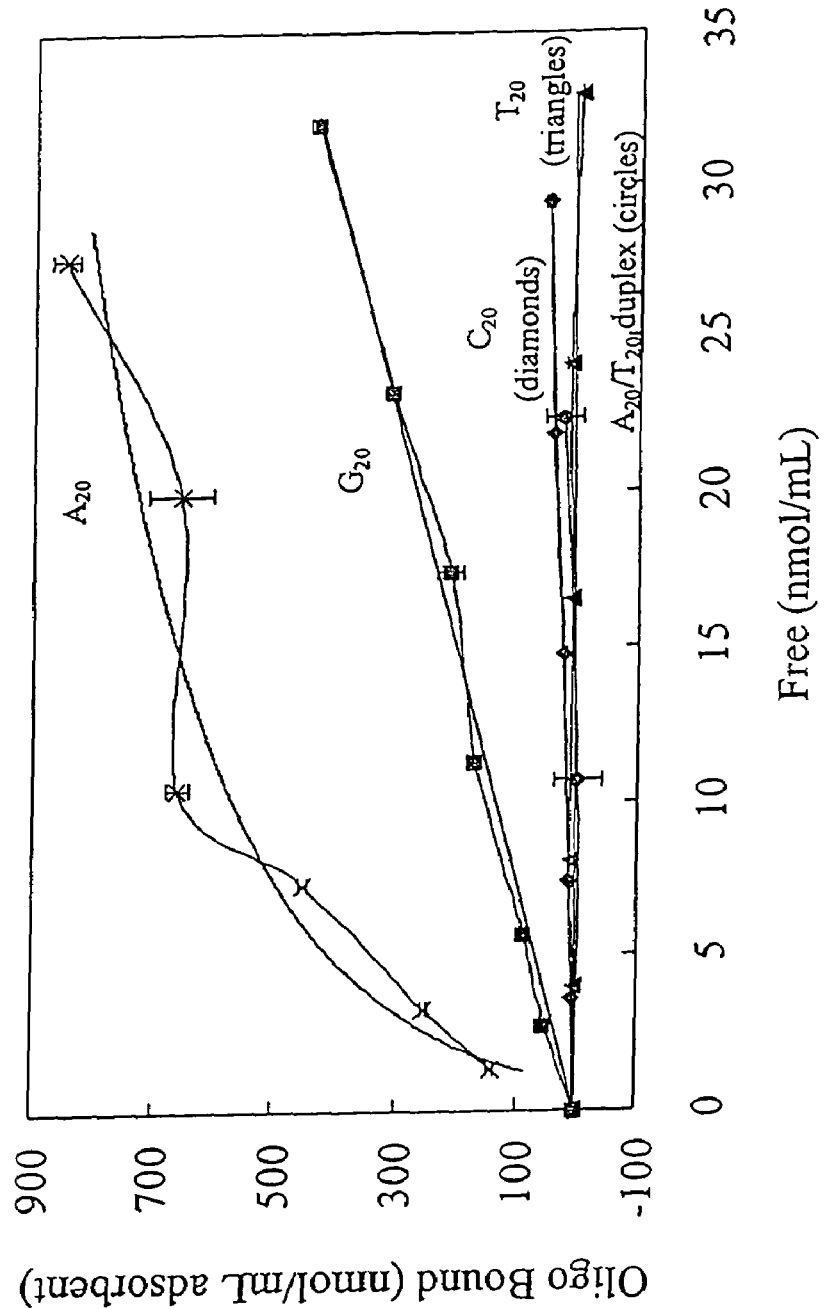
FIG. 4 graphs equilibrium adsorption isotherms of 20-mer homopolymer oligodeoxynucleotides on Ni(II) charged Chelating Sepharose matrix with 250 mM NaCl in 20 mM HEPES at pH 7.0.

The relative IMAC affinities of the nucleic acid bases in polynucleotides were examined using 20-mer oligodeoxynucleotide homopolymer isotherms on Ni(II)-charged IDA-Sepharose (FIG. 4). A20 bound with the highest affinity while G20 had an affinity approximately 10 times lower (based on a Langmuir fit). The affinities of the pyrimidines were much lower than those of the purines (approximately 60-and 300-fold lower affinity than A20 for C20 and T20 respectively). In addition, the A20/T20 heteroduplex had no detectable binding affinity, eliminating the phosphate backbone as a major source of adsorption affinity. The relative affinities of the homopolymers confirmed the nucleotide monomer results of Fanou-Ayi and Vijayalakshmi (11) and Hubert and Porath (12).

Plasmid Purification

Purification of plasmid DNA is an added advantage of IMAC. Previous work on affinity precipitation of DNA by compaction agents (19) allows for the creation of high purity plasmid preparation without the use of column chromatography. The major contaminant left in the plasmid DNA purified by compaction precipitation is contaminating RNA and linear DNA (1-5%). The IMAC separation technique of this invention is well-suited to bind the remaining RNA (the minor component) and DNA fragments to further purify large quantities of plasmid DNA on relatively small IMAC columns.

Figure 5:
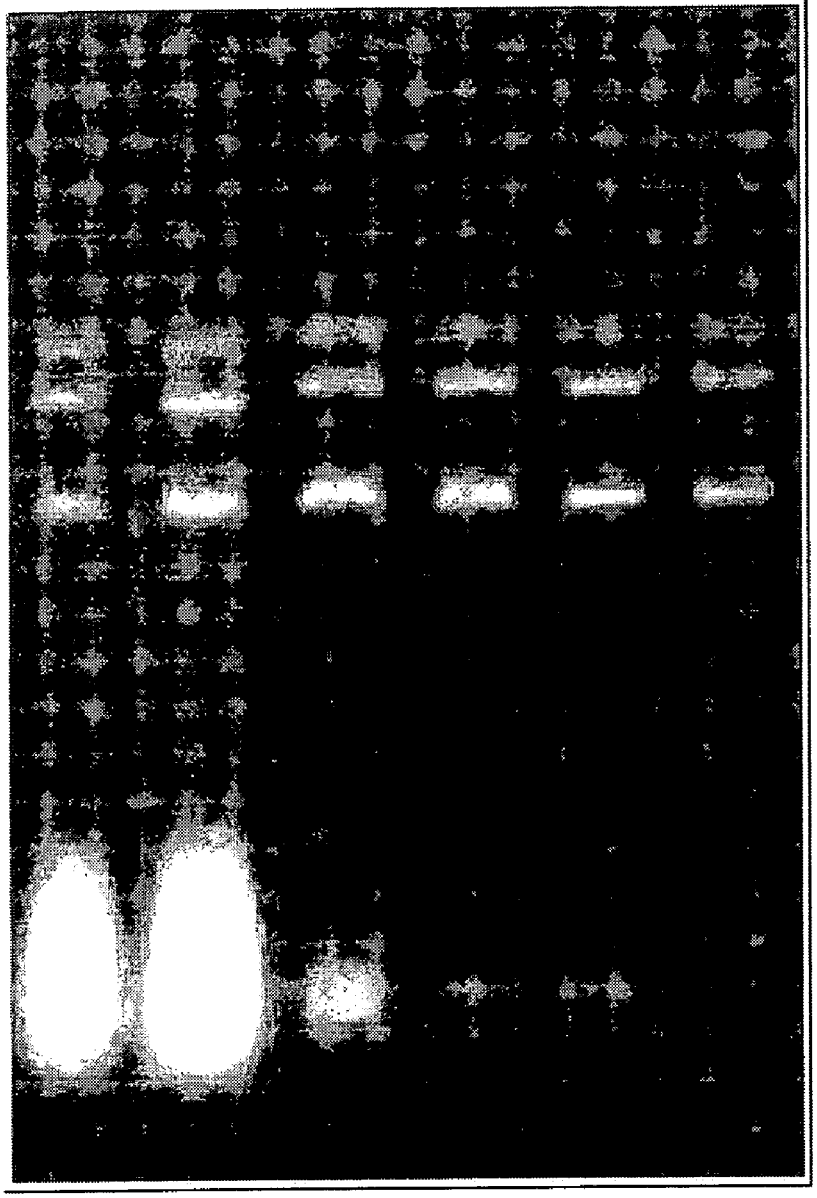
FIG. 5 shows repeated Cu IDA stripping of RNA from plasmid. EtBr stained 1% agarose gel of Cu (II) charged Chelating Sepharose matrix batch adsorption experiment of alkaline lysed *E. coli* with plasmid pBGS19luxwt. Lane 1 is the original lysate; Lane 2 is lysate contacted with non-charged IDA matrix; Lane 3 is the unbound material after a single batch adsorption; Lane 4 is Lane 3 after exposure to fresh matrix, Lane 5 similarly is Lane 4 after exposure to fresh matrix and Lane 6 is Lane 5 after exposure to fresh matrix.

FIG. 5 shows repeated Cu IDA stripping of RNA from plasmid. EtBr stained 1% agarose gel of Cu (II) charged Chelating Sepharose matrix batch adsorption experiment of alkaline lysed *E. coli* with plasmid pBGS19luxwt. Lane 1 is the original lysate; Lane 2 is lysate contacted with non-charged IDA matrix; Lane 3 is the unbound material after a single batch adsorption; Lane 4 is Lane 3 after exposure to fresh matrix, Lane 5 similarly is Lane 4 after exposure to fresh matrix and Lane 6 is Lane 5 after exposure to fresh matrix.

Figure 6:
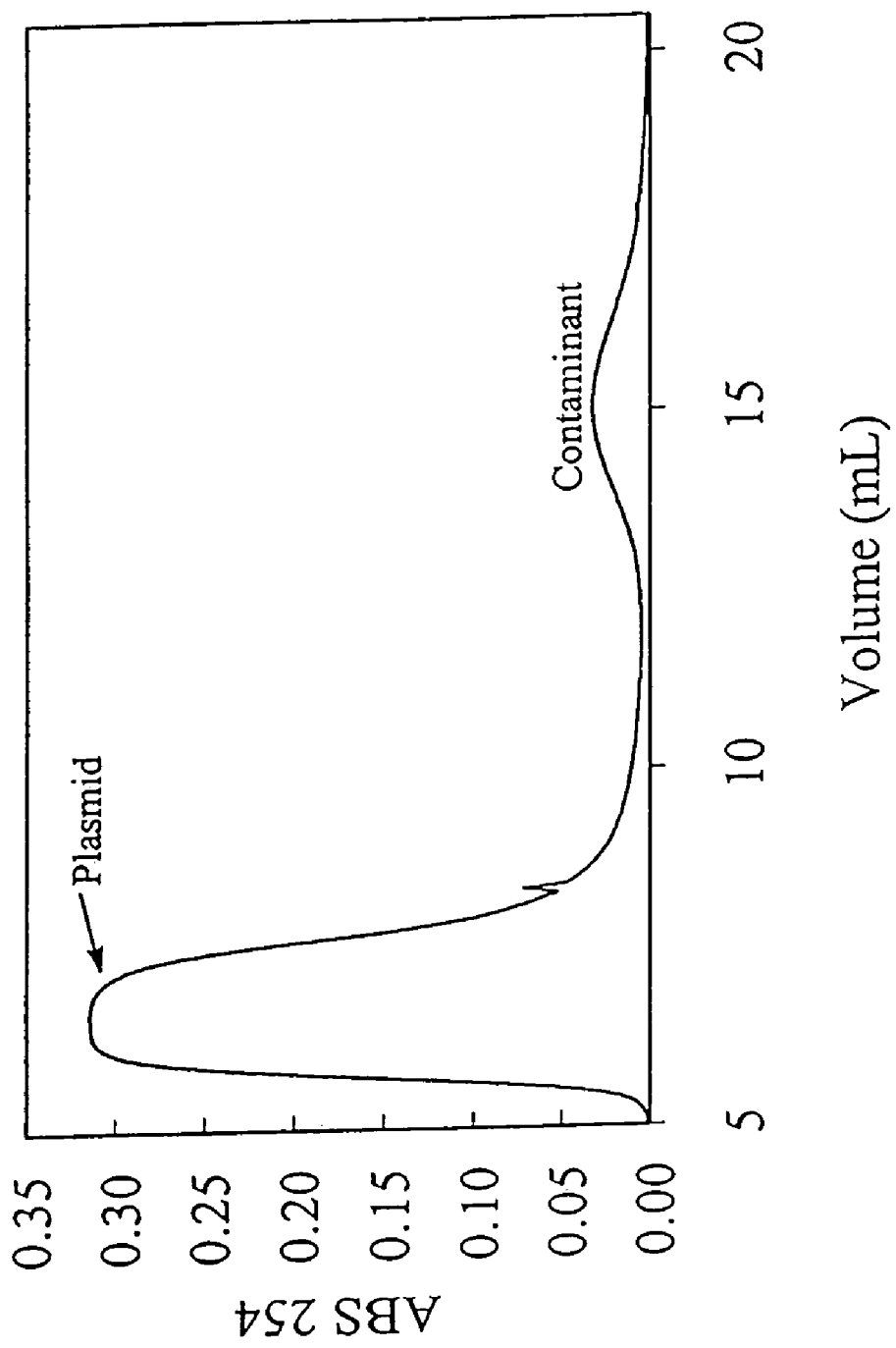
FIG. 6 shows a plasmid separation on Cu (II) charged IMAC. The plasmid pCMV sport β gal was ran over a 20 mL Cu (II) charged IMAC column (1×15 cm Amicon FPLC column packed with Chelating Sepharose Fast Flow) in a 20 mM HEPES with 250 mM NaCl at pH 7.0 running buffer (no gradient) at a flow rate of 2 mL/minute. The plasmid passed through the column with no hold-up while RNA and other damaged nucleic acids bind to the IMAC media and were retained on the column longer (isocratic separation). Nucleic acids were detected by gel electrophoresis and RNA was not visible on the 0.8 agarose gels.

The next step was to run a lysate over a column. Using compaction precipitation purified plasmid, column tests were done using a FPLC system. FIG. 6 shows the chromatogram of plasmid lysate purification using a 20 mL IMAC column charged with Cu (II). The plasmid initially passes through the column with no contaminating RNA as determined by gel electrophoresis and 260/280 ratios. In the end, IMAC worked well as a fast and efficient means of stripping RNA from a plasmid containing lysates.

RNA Separation

Figure 7:
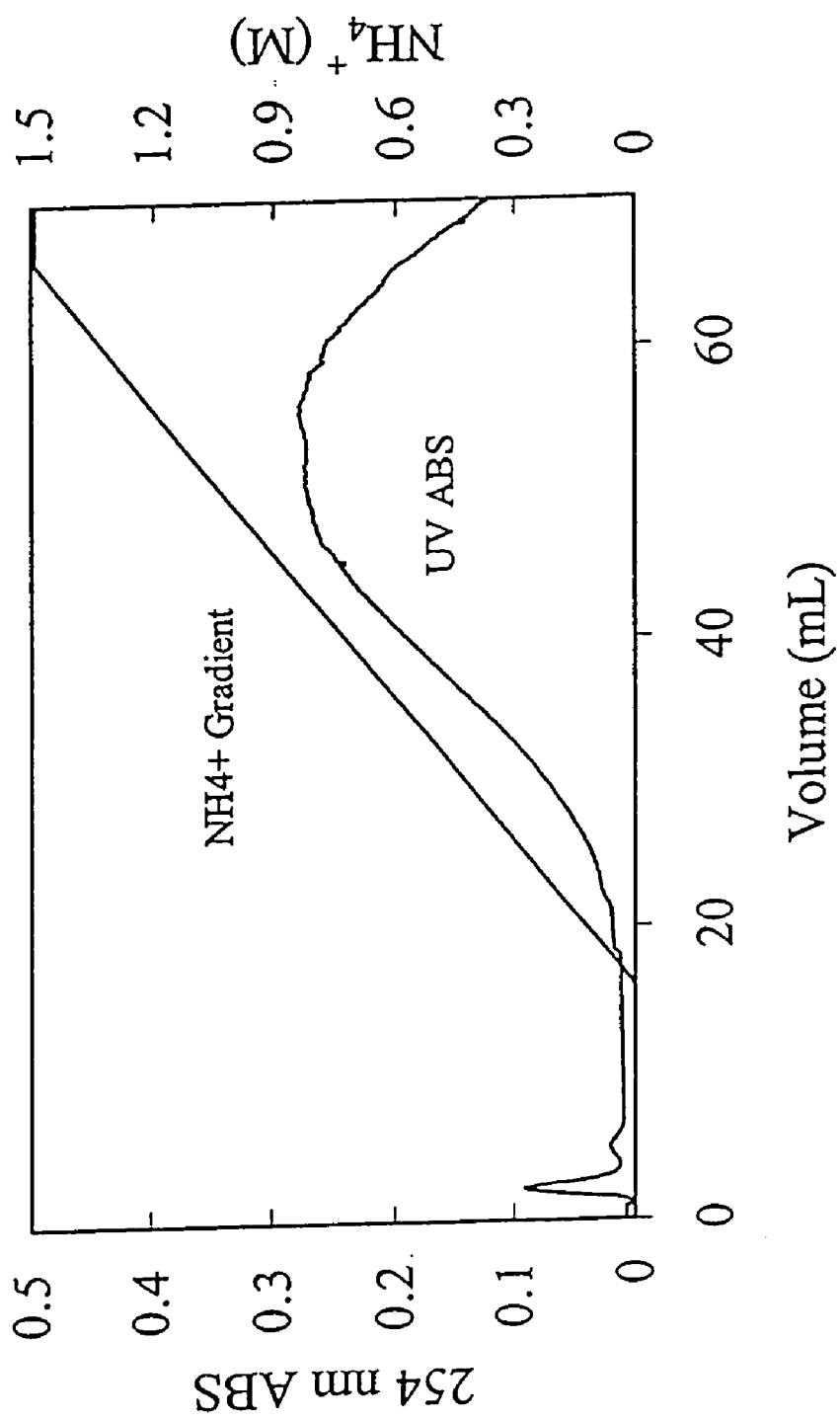
FIG. 7 shows a FPLC Chelating Sepharose separation of β ribozyme after compaction precipitation. The FPLC chromatogram traces the binding of β ribozyme to a 2 mL HyTrap Chelating Sepharose Column (2 chelating Sepharose 1 mL columns in series) and the subsequent elution. The ribozyme was loaded in column running buffer and a gradient was run from 0 to 1.5 M $NH_4Cl$.

RNA, purified by compaction precipitation, was separated via IMAC columns (1 mL Hytrap chelating column). FIG. 7 shows the FPLC trace of the separation of the b ribozyme by Cu (II) charged IMAC. The bound RNA was eluted in the figure by ammonium chloride, but elution can also be accomplished by using EDTA, pH, imidazole, or histidine. The ability to bind RNA and elute by direct base interaction to the IMAC media leads to a separation that operates on a different principle than anion exchange, hydrophobic interaction, and sizing chromatography.

Plasmid and RNA Separation

Figure 8:
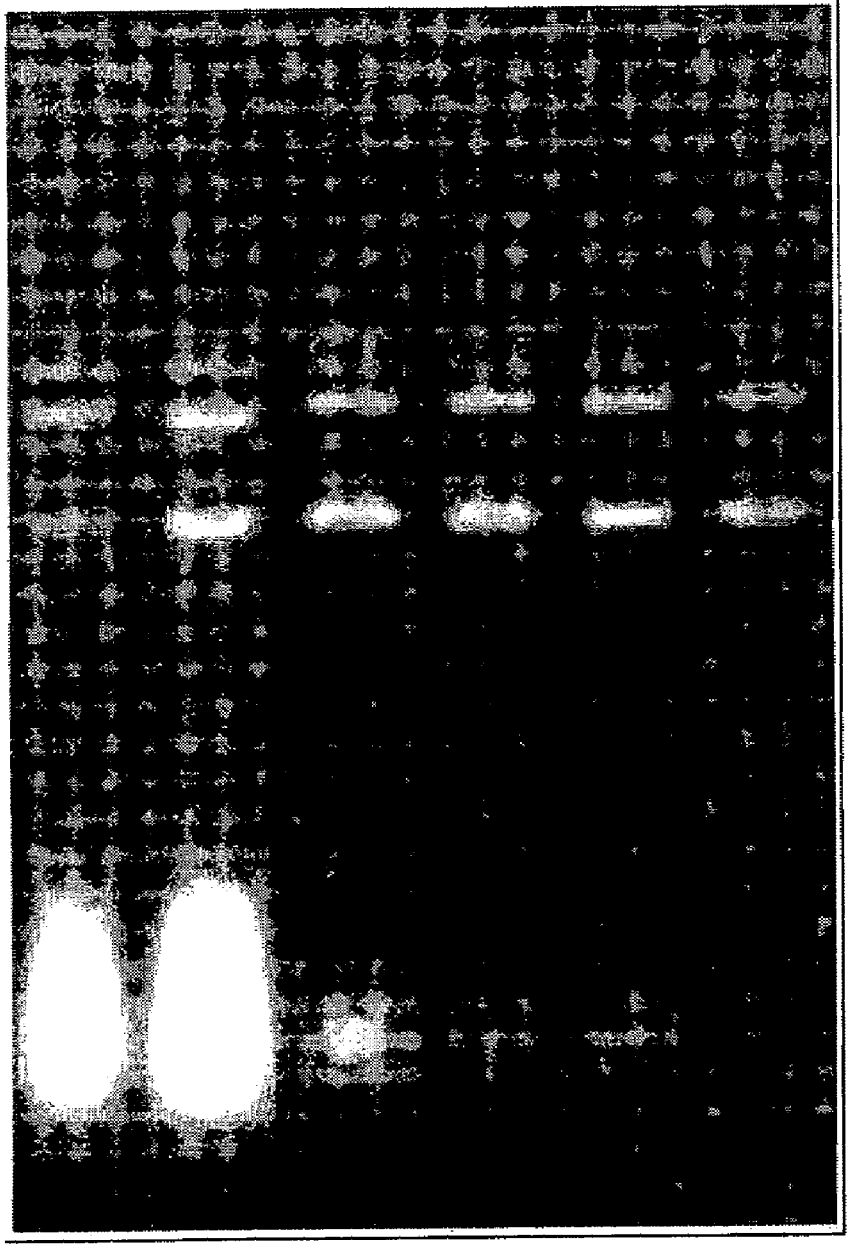
FIG. 8 shows repeated Cu(II) IDA stripping of RNA from a plasmid DNA-containing alkaline lysate. Ethidium bromide stained 1% agarose gel of Cu(II)-charged Chelating Sepharose batch adsorption of *E. coli* alkaline lysate with plasmid pBGS19luxwt. 1 mL of an IPA-precipitated alkaline lysate resuspended in 1 mL IMAC running buffer was contacted with 50 mL of Chelating Sepharose per batch experiment. Lane 1 is the original lysate; Lane 2 is lysate contacted with metal-free IDA matrix; Lane 3 is the unbound material after a single batch adsorption with Cu(II)-charged matrix; and, each of Lanes 4-6 is the previous lane after exposure to fresh matrix.

The nucleic acid discrimination achieved with IMAC suggests application of the method to the purification of plasmid DNA from RNA-rich bacterial lysates FIG. 8 shows repeated Cu(II) IDA stripping of RNA from a plasmid DNA-containing alkaline lysate. Ethidium bromide stained 1% agarose gel of Cu(II)-charged Chelating Sepharose batch adsorption of *E. coli* alkaline lysate with plasmid pBGS19luxwt. 1 mL of an IPA-precipitated alkaline lysate resuspended in 1 mL IMAC running buffer was contacted with 50 uL of Chelating Sepharose per batch experiment. Lane 1 is the original lysate; Lane 2 is lysate contacted with metal-free IDA matrix; Lane 3 is the unbound material after a single batch adsorption with Cu(II)-charged matrix; and, each of Lanes 4-6 is the previous lane after exposure to fresh matrix.

Figure 9:
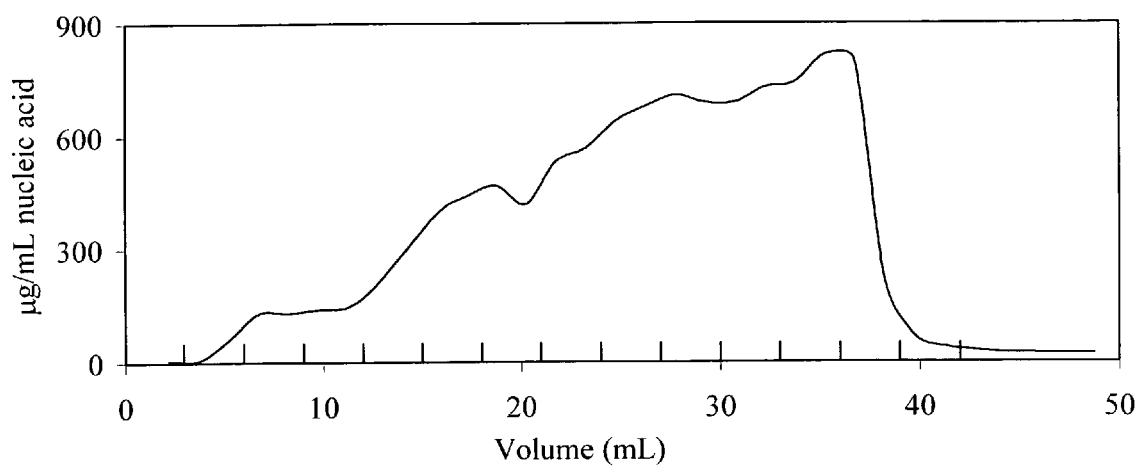
FIG. 9 shows (Top) FPLC chromatogram of an alkaline lysate containing pCMV sport b gal plasmid DNA run over a 15 mL Cu(II)-charged Chelating Sepharose column. Approximately 30 mL of lysate containing 3.8 mg/mL of nucleic acid was passed over the column at 1.5 mL/min. (Bottom) 0.8% E gel (Invitrogen) stained with SYBR Gold to visualize each fraction from the FPLC run. The fractions on the upper plot correspond to the lanes in the gel below.
Figure 9:
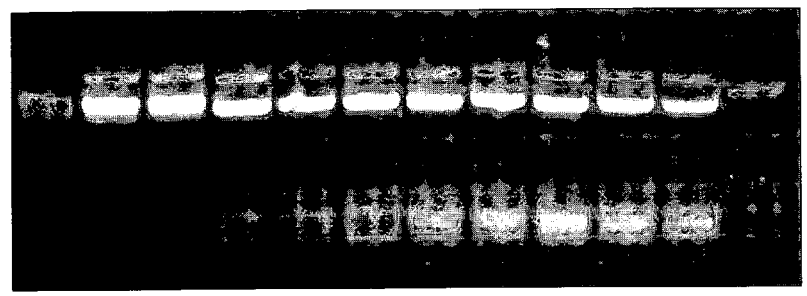

IMAC column chromatography was used to strip RNA from an E. coli alkaline lysate containing the plasmid pCMV sport b gal. FIG. 9 shows an E. coli alkaline lysate purified using a 20 mL Cu(II)-charged IDA Sepharose column. The plasmid initially passed through the column with an undetectable amount of contaminating RNA as determined by gel electrophoresis and 260/280 ratio. Initial RNA breakthrough was observed when 1 mg/mL of RNA was bound. Approximately 80% of the contaminating RNA was still bound at a loading capacity of 5 mg/mL.

Previous work on affinity precipitation of DNA from RNA by compaction agents (19) allows for the preparation of a high purity plasmid DNA without the use of column chromatography. The major contaminant in the plasmid DNA purified by compaction precipitation is RNA. IMAC adsorption has a high capacity for polishing of compaction precipitated DNA by selective adsorption of the minor RNA component.

RNA (b ribozyme), purified by compaction precipitation (20), was separated on a 1 mL Cu(II)-charged Hytrap chelating column (not shown) using an 0 to 2 M ammonium chloride gradient. The ability to bind RNA leads to an IMAC separation that operates on a different principle than anion-exchange, hydrophobic-interaction, boronate, and size-exclusion chromatography, allowing orthogonal separations.

PCR Product Cleanup

Figure 10:
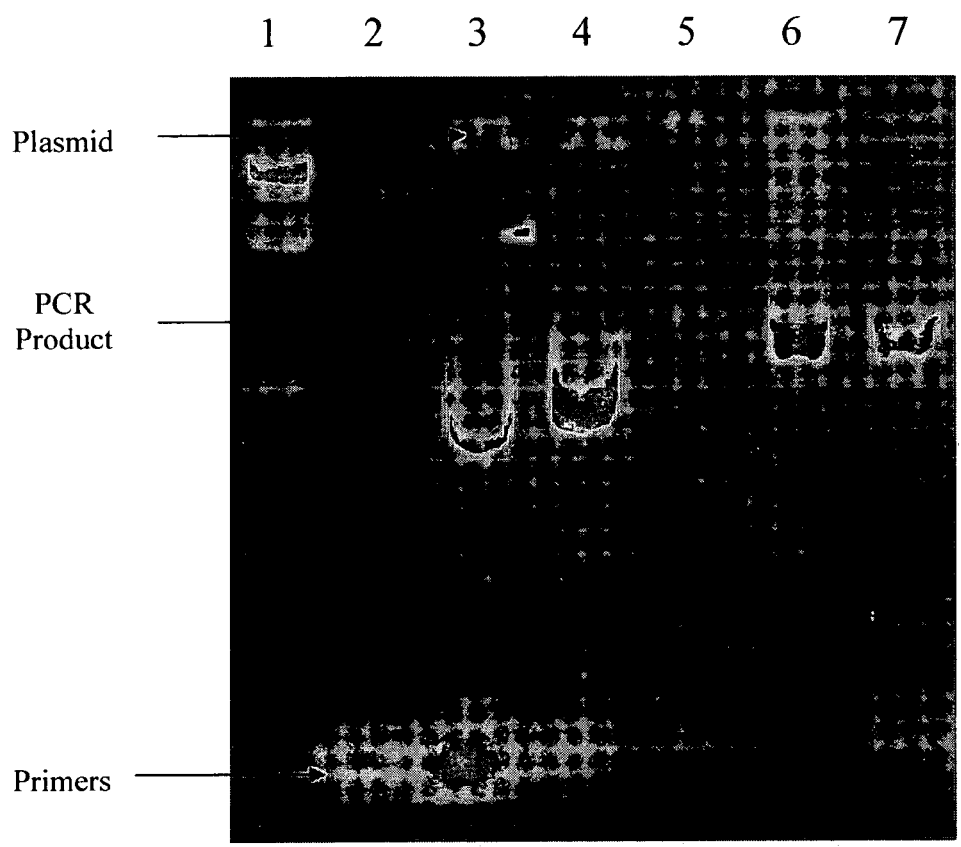
FIG. 10 shows 2% agarose gel stained with SYBR Gold nucleic acid stain (Molecular Probes) of PCR product cleanup. Lane 1 is the 1 kb ladder; Lane 2 is PCR primers (forward and reverse) for the plasmid pCMV sport b gal (Gibco); Lane 3 is an PCR reaction amplifying an ~800 bp fragment of pCMV sport b gal; Lane 4 is the unpurified PCR product ran through a Ni (II) charged spin column; Lane 5 is the elution of the Ni (II) charged spin column from Lane 4 (eluted with 500 mM imidazol in column running buffer); Lane 6 is the unpurified PCR product ran through a Cu (II) charged spin column; and Lane 7 is the elution of the Cu (II) charged spin column from Lane 6 (eluted with 500 mM imidazol in column running buffer)

This example illustrates the utility of this invention in a model PCR reaction system. PCR product cleanup was performed using IMAC spin columns directly with PCR products. The PCR reactions were loaded directly onto the spin columns allowing for the rapid removal of PCR primers and stunted fragments. FIG. 10 shows a 2% agarose gel of the cleanup of a PCR product using a Ni (II) charged IMAC spin column. The spin column mainly left behind the double-stranded PCR product and the plasmid DNA template as seen in lane 4 of FIG. 10. In addition, other metal ions were evaluated for this application. Cu (II) binds, not only the primers and fragments, but also the PCR product itself. Because of its high affinity for aromatic nitrogens, copper is thought to bind to the ragged ends commonly left by Taq polymerase. Thus, the present invention is also related to the direct binding and elution of the PCR fragments.

PCR Product Purification

Figure 11:
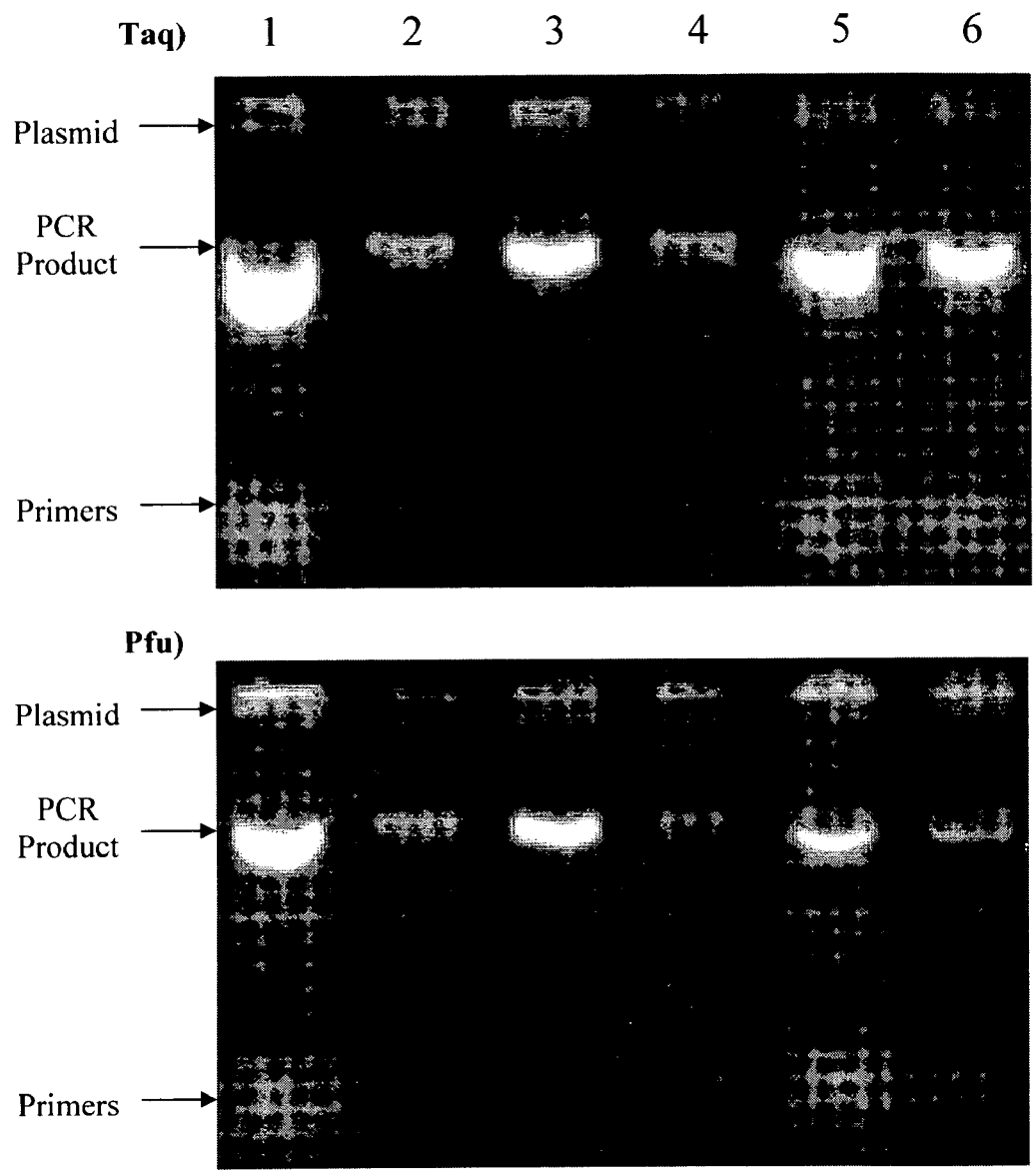
FIG. 11 shows PCR product cleanup by IMAC. Upper) 1.5% agarose gel stained with SYBR Gold nucleic acid stain (Molecular Probes). Lane 1 is an overload (approx. 1300 ng) of Taq PCR reaction amplifying an 800 bp fragment of pCMV sport b gal; Lane 2 is a diluted loading (200 ng) of Lane 1; Lane 3 is overload (200 ng) PCR product mixture from Lane 1 run through a Cu(II) charged spin column; Lane 4 is a diluted loading (30 ng) of Lane 3; Lane 5 is an overload of the elution of the Cu(II) charged spin column from Lane 3-4 with 500 mM imidazole with 250 mM NaCl in 20 mM HEPES at pH 7.0; and, Lane 6 is a 2-fold dilution loading of Lane 5. Lower) 1.5% agarose gel stained with SYBR Gold nucleic acid stain (Molecular Probes) the same as the upper panel except Pfu polymerase was used in the PCR reactions.

PCR reaction mixtures were loaded directly onto Cu(II)-charged, 100 mL spin columns for rapid removal of primers and stunted or mismatch-containing products. The IMAC column captured the primers and the defective products leaving primarily the double-stranded PCR product and the plasmid DNA template (FIG. 11 top and bottom, Lane 3). Partial elution (FIG. 11 top, Lane 5) shows that the column binds not only the primers and fragments, but also the Taq PCR product itself, presumably through mismatched bulges or the 3'A overhang commonly left by Taq polymerase. However, processing of a Pfu (21) polymerase PCR reaction product mixture amplifying the same sequence gave similar results (FIG. 11 bottom, Lane 5), but products of this proofreading polymerase were not as readily retained on the IMAC column. When the PCR product band in the elutant lanes of the gels were integrated, 1.6 times as much PCR product was retained on the IMAC column when Taq polymerase PCR reactions were purified vs. Pfu PCR reactions. In addition, when the IMAC purified Taq PCR product was sequenced improved fidelity was seen over a non-IMAC purified control sample (results not shown).

Mismatch Detection Using IMAQ

Figure 12:
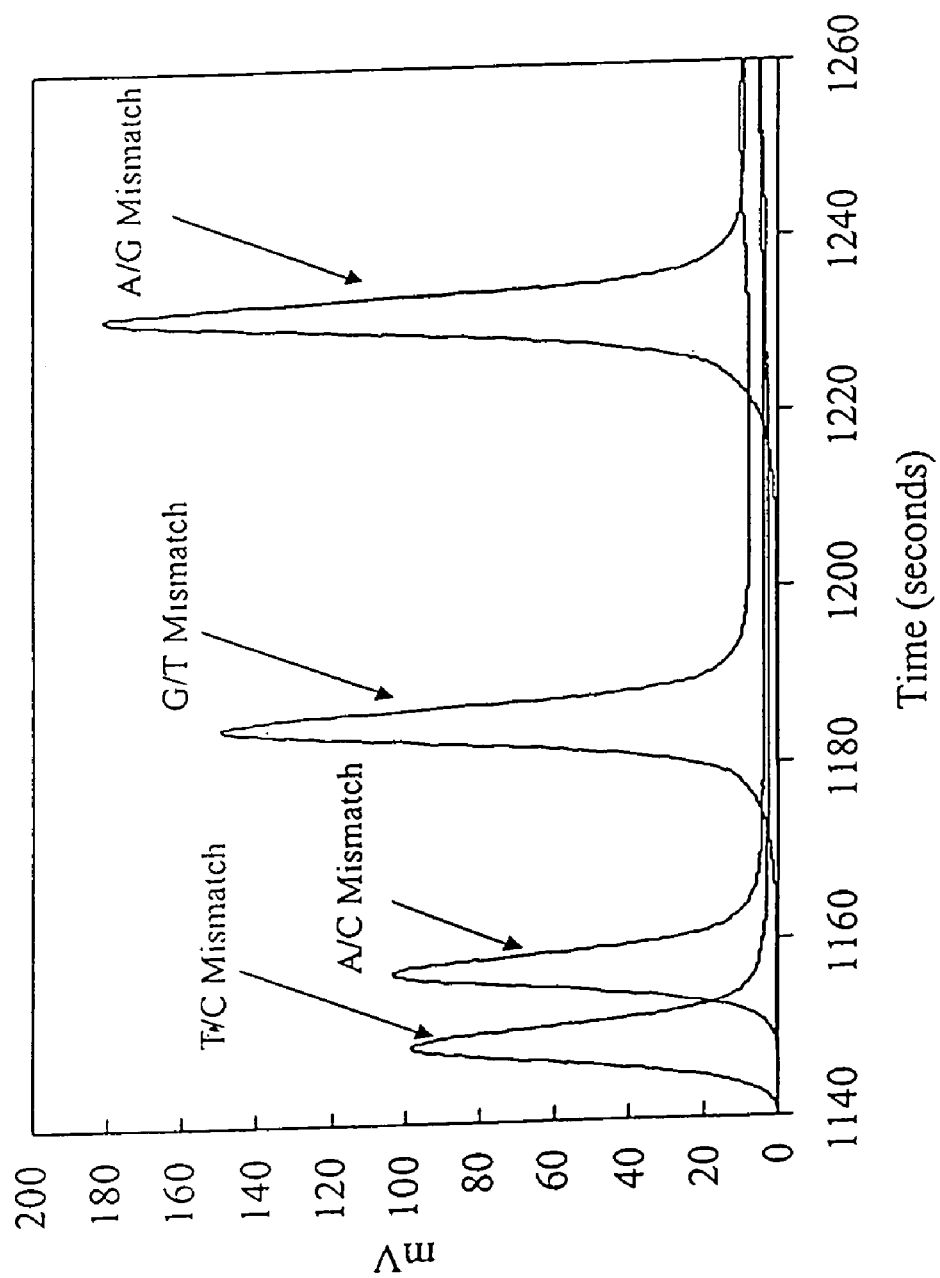
FIG. 12 shows a HPLC chromatogram of 20-mer oligodeoxynucleotide heteroduplexes bearing the internal mismatches T/C, G/T, A/C, and A/G. The gradient was run over 21 mL (at 1 mL/min) from 0 mM imidazole to 40 mM imidazole in 20 mM HEPES with 250 mM NaCl on a 7 mm×7 cm Toso Haas Metal Chelating HPLC column charged with Cu(II)

Higher resolution IMAC HPLC can separate mismatch-bearing oligonucleotide heteroduplexes, presumably through interactions with bases in the disordered region. As shown in FIG. 12, retention correlates well with the binding affinities of the homopolymers (FIG. 4). Especially with the enhanced resolution of metal affinity capillary electrophoresis (22), this mismatch separation could serve as the basis of PCR product cleanup, SNP scoring, or hybridization assays. Fragmentation of a potentially mutated gene followed by heat denaturation and reannealing in the presence of the corresponding wild type DNA, could allow efficient DNA sequence confirmation by IMAC in an analysis similar to "tryptic mapping" of proteins.

CONCLUSIONS

IMAC, a robust and widely used chromatographic process, and now represents an effective nucleic acid separation technique with many applications. Metal charged IMAC ligands have affinity for single-stranded nucleic acids, in particular exposed nucleic acid bases or other molecules including at least one non-shielded purine or pyrimidine moiety. Through isotherm measurement, the IMAC matrix has been proven to bind to the nucleic acid bases and not the phosphate anion backbone or the ribose in the backbone. The aromatic nitrogens in the nucleic acid bases are the targets of the metal ion interaction meaning that purines have a higher affinity than pyrimidines for the charged IMAC matrix. The determined order of affinities are $A > G >> C \geq T$.

The nitrogen containing aromatic bases can be effectively stripped from a bacterial lysate or free solution. One preferred application of IMAC described herein is the purification of plasmid DNA by retaining RNA contaminants. In addition, separation of RNA (b ribozyme), single-stranded nucleic acids, and primers, truncated fragments and bases can be easily be removed from sequencing/PCR reactions.

Chelated soft metal ions interact with exposed bases of nucleic acids, and this interaction can serve as the basis of a variety of preparative and analytical methods useful in genetic technology. In addition, to those demonstrated here, further applications may include eukaryotic (poly(A) tailed) mRNA isolation, improvement of the quality and clonability of PCR products, and economical SNP scoring and sequence confirmation.

Detailed Description of Apparatuses of This Invention

Figures 13A, 13B:
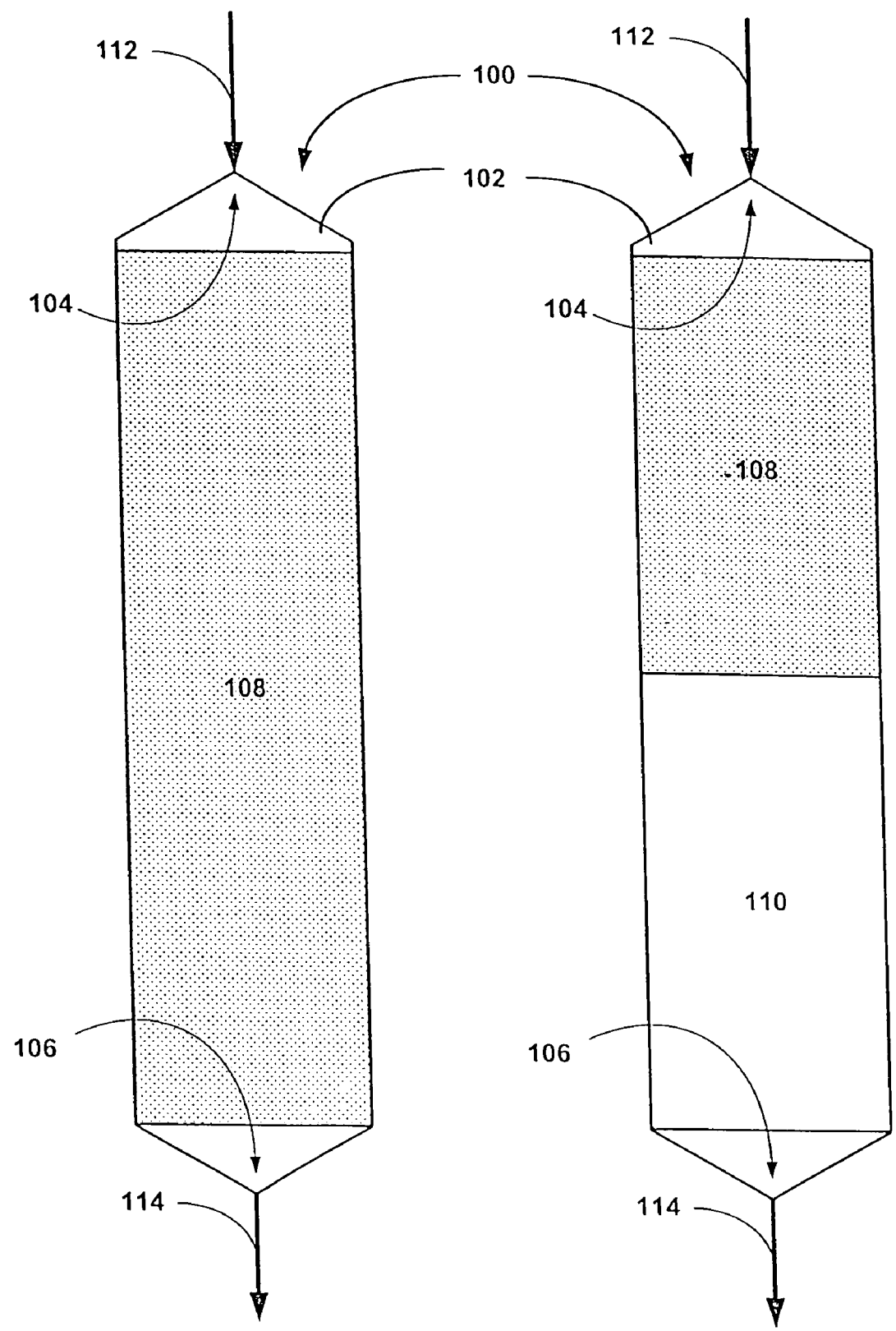
FIGS. 13A&B depict preferred embodiments of an apparatus of this invention.

Referring now to FIGS. 13A&B, two preferred embodiments of separation apparatus of this invention, generally 100, are shown to include a column 102 having an inlet 104 adapted to receive a sample (not shown), an outlet 106 and a single zone 108, while the column 102 of FIG. 13B includes a first zone 108 and a second zone 110. The single or first zone 108 includes an IMAC matrix with one or more immobilized metal atoms and/or ions bound thereto, while the second zone includes another matrix capable of separating sample components based on a different chemical and/or physical property such as size, charge, hydrophobicity, hydrophilicity, or any other property. Of course, one of ordinary skill in the art should recognize that the two zones in FIG. 13B can be two different columns connected together in series.

The apparatus 100 is utilized by supplying a sample or sample flow 112 to the inlet 104 and analyzing an apparatus effluent 114 leaving the outlet 106. The sample or sample flow 112 can be a single sample or the output of an upstream separation apparatus. Moreover, the apparatus 100 can be used in a discrete or continuous mode of operation depending on the nature of the analysis intended.

Figure 14:
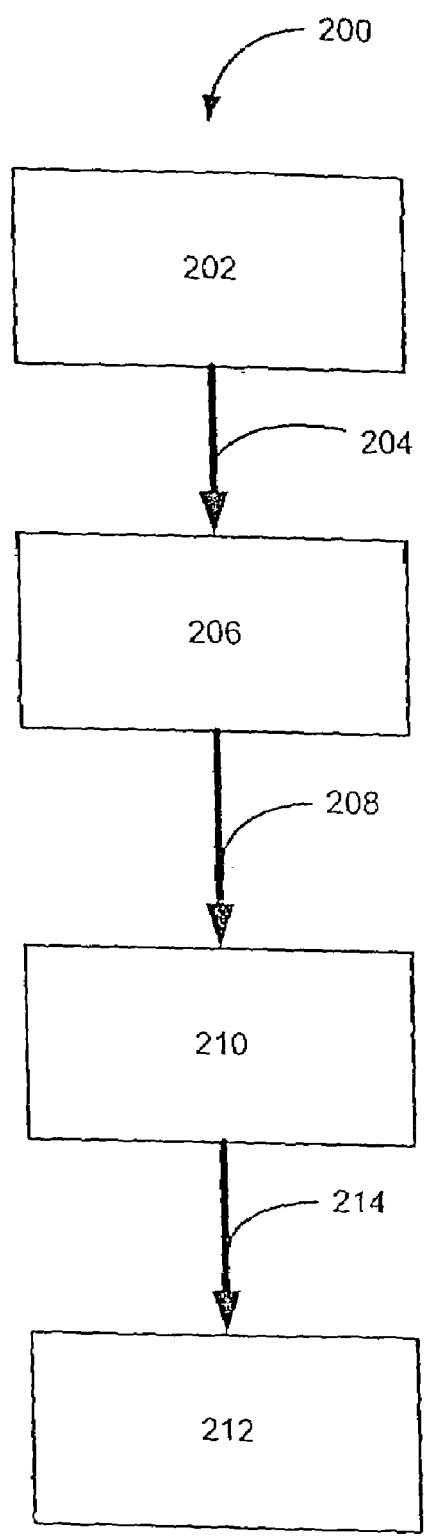
FIG. 14 depicts another preferred embodiment of an apparatus of this invention.

Referring now to FIG. 14, a preferred embodiment of an analytical instrument apparatus of this invention, generally 200, is shown to include a sample input unit 202 in fluid communication via a first fluid conduit 204 with a separation unit 206. The separation unit 204 includes at least one separation apparatus of FIGS. 13A&B. The separation unit 204 is in fluid communication via a second fluid conduit 208 with a detector unit 210. The detector unit 210 is adapted to convert one or more properties of an effluent of the separation unit 206 to a signal. The signal is forwarded to an analyzer unit 212 via an electric conduit 214, which places the detector unit 210 in electrical communication with the analyzer unit 212. The analyzer unit 212 converts the signal produced by the detector unit 210 into a measurement of the detected property. Of course, the detector unit 210 and the analyzer unit 212 can be a single unit. Generally, the analyzer unit 212 is a digital processing unit including a memory, a digital processor, output devices such as a printer, a CRT, or the like and associated software and hardware for communication, storage, retrieval and human interaction.

The sample input unit 202 can be an injector unit for injecting or introducing a single sample or plug of sample into the separation unit 206

The term fluid communication means that fluid is able to flow from one unit to the other unit in the indicated direction. The term electrical communication means that an electric signal travels from one unit to another unit in the indicated direction.

Modifications

While not to be taken as limiting, the following embodiments are also to be included within the inventions:

A composition comprising a first compound including immobilized metal atoms and/or ions capable of binding compounds containing a non-shielded purine or pyrimidine group and a second compound containing a non-shielded purine or pyrimidine group bound to a portion of the metal atoms and/or ions; wherein the second compound is selected from the group of RNA, single stranded DNA, and other molecules having a non-shielded purine and/or pyrimidine moiety or group, or wherein the first compound comprises a polymeric material including a plurality of ligands bonded thereto, each ligand immobilizing a metal ion selected from the group consisting of $Cu^{2+}$, $Zn^{2+}$, $Ni^{2+}$, $Fe^{3+}$, $Fe^{2+}$, $Co^{2+}$, $Sc^{2+}$, $Ti^{2+}$, $V^{2+}$, $Cr^{2+}$, $Mn^{2+}$, $Ca^{2+}$, $Cd^{2+}$ or $Hg^{2+}$ or mixtures or combinations thereof, or wherein the metal ion selected from the group consisting of $Cu^{2+}$, $Zn^{2+}$, $Ni^{2+}$, $Fe^{2+}$, or $Co^{2+}$ or mixtures or combinations thereof.

An immobilized metal affinity chromatography (IMAC) column comprising a packing including immobilized metal atoms and/or ions capable of binding compounds containing a non-shielded purine or pyrimidine moiety or group and a compound containing a non-shielded purine or pyrimidine moiety or group bound to a portion of the metal atoms and/or ions wherein the second compound is selected from the group of RNA, single stranded DNA, and other molecules having a non-shielded purine and/or pyrimidine moiety or group; or wherein the first compound comprises a polymeric material including a plurality of ligands bonded thereto, each ligand immobilizing a metal ion selected from the group consisting of $Cu^{2+}$, $Zn^{2+}$, $Ni^{2+}$, $Fe^{2+}$, $Fe^{2+}$, $Co^{2+}$, $Sc^{2+}$, $Ti^{2+}$, $V^{2+}$ $Cr^{2+}$, $M^{2+}$, $Ca^{2+}$, $Cd^{2+}$ or $Hg^{2+}$ or mixtures or combinations thereof; or wherein the metal ion selected from the group consisting of $Cu^{2+}$, $Zn^{2+}$, $Ni^{2+}$, $Fe^{2+}$, or $Co^{2+}$ or mixtures or combinations thereof.

A substrate comprising a plurality of ligands bonded thereto, each ligand immobilizing a metal atom and/or ion capable of binding compounds containing a non-shielded purine or pyrimidine moiety or group, and a compound containing a non-shielded purine or pyrimidine moiety or group bound to a portion of the metal atoms and/or ions wherein the second compound is selected from the group of RNA, single stranded DNA, and other molecules having a non-shielded purine and/or pyrimidine moiety or group; or wherein the first compound comprises a polymeric material including a plurality of ligands bonded thereto, each ligand immobilizing a metal ion selected from the group consisting of $Cu^{2+}$, $Zn^{2+}$, $Ni^{2+}$, $Fe^{3+}$, $Fe^{2+}$, $Co^{2+}$, $Sc^{2+}$, $Ti^{2+}$, $V^{2+}$, $Cr^{2+}$, $Mn^{2+}$, $Ca^{2+}$, $Cd^{2+}$ or $Hg^{2+}$ or mixtures or combinations thereof; or wherein the metal ion selected from the group consisting of $Cu^{2+}$, $Zn^{2+}$, $Ni^{2+}$, $Fe^{2+}$, or $Co^{2+}$ or mixtures or combinations thereof; or wherein the substrate is selected from the group consisting of a polymer, a column inner wall, a membrane, an inorganic support, a metallic support, and a surface of an electronic chip.

An apparatus comprising a sample input unit, a separation unit, a detector unit and an analyzer unit wherein the separation unit is a zone comprising an IMAC matrix including metal atoms, metal ions or mixtures thereof capable of binding compound having a non-shielded purine moiety, pyrimidine moiety or mixture thereof; or wherein the zone is a column; or wherein the separation unit comprises a first zone comprising a IMAC matrix including metal atoms, metal ions or mixtures thereof capable of binding compound having a non-shielded purine moiety, pyrimidine moiety or mixture thereof and a second zone comprising a second matrix capable of separating compounds based on at least one chemical or physical property; or wherein the second matrix comprises an anion exchange material or an HIC material; wherein the first and second zones are a columns connected in series; or wherein the first zone comprises a first portion of a column and the second zone comprises a second portion of the column.

An apparatus comprising a substrate having an IMAC ligand coated thereon, bonded thereto, deposited thereon or deposited therein, where the substrate is adapted to remove contaminating compounds including a non-shielded purine moiety, pyrimidine moiety, or mixture thereof from target compounds including a shielded purine moiety, pyrimidine moiety, or mixture thereof wherein the substrate is selected from the group consisting of a porous stirrer, a filter, a membrane, an interior wall of a vessel, or mixtures thereof; or wherein the contaminating compounds are RNA and target compounds are plasmids.

A method for separating compounds comprising the step of:

contacting a solution comprising compounds including a non-shielded purine or pyrimidine moiety and compounds including a shielded purine or pyrimidine moiety with a solid composition including immobilized metal atoms and/or ions capable of binding compounds containing a non-shielded purine or pyrimidine moiety to form a supernatant liquid having a reduced amount of compounds including a non-shielded purine or pyrimidine moiety; further comprising the step of:

separating the supernatant liquid from the solid composition; or further comprising the steps of:

separating the supernatant liquid from the solid composition and eluting the compounds including a non-shielded purine or pyrimidine moiety from the solid composition; or wherein the compounds including a non-shielded purine or pyrimidine moiety comprise a nucleoside, a nucleotide, a single stranded nucleic acid oligomer, or a single stranded nucleic aid polymer and the compounds including a shielded purine or pyrimidine moiety comprise double stranded nucleic acid oligomers or double stranded nucleic acid polymers; or wherein the supernatant liquid comprises compounds including a shielded purine or pyrimidine moiety having less than or equal to 5% by weight compounds including a non-shielded purine or pyrimidine moiety; or wherein the supernatant liquid comprises compounds including a shielded purine or pyrimidine moiety having less than or equal to 1% by weight compounds including a non-shielded purine or pyrimidine moiety; or wherein the supernatant liquid comprises compounds including a shielded purine or pyrimidine moiety having less than or equal to 0.01% by weight compounds including a non-shielded purine or pyrimidine moiety.

A method for making multisubstrate columns comprising the step of running a small amount of IMAC ligand onto an activated column and then flooding the rest of the column with at least one additional ligand or stationary phase.

A method for separating compounds comprising the steps of:

passing a solution comprising a mixture of compounds including a non-shielded purine moiety, a non-shielded pyrimidine moiety or mixture thereof through a column including an IMAC ligand, where the ligand is capable of differentially binding the compounds; and collecting purified samples of each compound; or further comprising the step of:

detecting each compound in an effluent from the column as a function of time from at least one detectable property associated with each compound; and determining the identity of each compound from the detected properties; or wherein the mixture of compounds comprises poly(A) tailed mRNA sequences and other mRNA sequences from eukaryotic cells, where the poly(a) mRNA sequences elute after the other mRNA sequences; or wherein the mixture for compounds comprises denatured nucleic acid sequences, where sequences having A rich regions elute after sequences having T rich regions so that complementary strands can be resolved; or wherein the mixture for compounds comprises denatured nucleic acid sequences, where sequences having C rich regions elute after sequences having G rich regions so that complementary strands can be resolved; or wherein the mixture of compounds comprises denatured nucleic acid sequences having A-C, A-G, A-C-G, T-G, T-C and or T-G-C rich regions so that the sequences having thee A-C, A-G, and/or A-C-G rich regions elute after their complementary sequences having T-G, T-C and or T-G-C rich regions resulting in a resolution of complementary sequences.

A method for purifying food stuffs containing purine and/or pyrimidine moieties comprising the steps of:

forming a crude food stuff comprising cellular constituents including digestable proteins and nucleic acid contaminants including a non-shielded purine moiety, a non-shielded pyrimidine moiety or mixture thereof;

contacting the food stuff with substrate comprising an IMAC ligand, where the substrate binds the nucleic acid contaminants; and removing the substrate comprising the IMAC ligand having bound thereto the nucleic acid contaminants to form a purified food stuff; further comprising the step of treating the crude food stuff with a DNAse, endo or exo nuclease or other nucleic acid digestion enzyme or agent prior to the contacting step.

A method for purifying a crude compound containing a non-shielded purine and/or pyrimidine moiety comprising the steps of:

forming a crude mixture comprising a target compound and contaminants;

contacting the crude mixture with an agent including an IMAC ligand capable of binding to the target compound to form an IMAC ligand complex;

separating the complex from the contaminants; and recovering the compound from the complex; wherein the compound is an AIDs drugs selected from the group consisting of AZT or DDI, co-enzyme A, or mixtures thereof.

An assay comprising the steps of:

contacting a microplate substrate comprising wells coated with a composition comprising a IMAC-oligonucleotide complex including an IMAC ligand and a single stranded oligonucleotide having a first molecular and/or atomic tag bound to the IMAC ligand; and contacting a nucleic acid sequence including a second molecular and/or atomic tag with the IMAC-oligonucleotide complex; and measuring a change in fluorescence when the nucleic acid sequence includes a complimentary subsequence to oligonucleotide due to an interaction between the first and second molecular and/or atomic tags; wherein the first tag is a fluorophore and the second tag is a quencher for the fluorophore; or wherein the second tag is a fluorophore and the first tag is a quencher for the fluorophore; or 2, wherein the tags for a fluorescent donor-acceptor pair.

An assay comprising the steps of contacting a substrate comprising a surface coated with a composition comprising an IMAC ligand and a first fluorophore with an oligonucleotide including a second fluorophore and measuring an effective Stoke shift such that a large effective Stoke shift signifies oligonucleotide binding to the coated substrate and a normal effective Stoke shift signifies no oligonucleotide binding to the coated substrate.

REFERENCES

1. Porath, J. (1992) *Protein Expr. Purif* 3, 263-281.
2. Porath, J., Carlsson, J., Olsson, I. & Belfrage, G. (1975) *Nature* 258, 598-599.
3. Alexandratos, S. D., Beauvais, R., Duke, J. R. & Jorgensen, B. S. (1998) *J. Appl. Polym. Sci.* 68, 1911-1916.
4. Yang, L., Jia, L., Zou, H. & Zhang, Y. (1999) *Biomed. Chromatogr.* 13, 229-234.
5. Nieba, L., Nieba-Axmann, S. E., Persson, A., Hamalainen, M., Edebratt, F., Hansson, A., Lidholm, J., Magnusson, K., Karlsson, A. F. & Pluckthun, A. (1997) *Anal. Biochem.* 252, 217-228.
6. Holmes, L. D., Serag, A. A., Plunkett, S. D., Todd, R. J. & Arnold, F. H. (1992) *Methods: A Companion to Methods in Enzymology* 4, 103-108.
7. Van Dam, M. E., Wuenschell, G. E. & Arnold, F. H. (1989) *Biotechnol. Appl. Biochem.* 11, 492-502.
8. Spiro, T, G. (1980) *Nucleic Acid—Metal Ion Interactions* (John Wiley, NY).
9. Kisko, J. L. & Barton, J. K. (2000) *Inorg. Chem.* 39, 4942-4949.
10. Jordan, P. & Carmo-Fonseca, M. (1998) *Nucleic Acids Res.* 26, 2831-2836.
11. Fanou-Ayi, L. & Vijayalakshmi, M. (1983) *Ann. N.Y. Acad. Sci.* 413, 300-306.
12. Hubert, P. & Porath, J. (1980) *J. Chromatogr.* 198, 247-255.

13. Min, C. & Verdine, G. L. (1996) *Nucleic Acids Res.* 24, 3806-3810.
14. Hermann, T. & Westhof, E. (1998) *Structure.* 6, 1303-1314.
15. Gonzalez, R. L., Jr. & Tinoco, I., Jr. (1999) *J. Mol. Biol.* 289, 1267-1282.
16. Walter, F., Murchie, A. I., Thomson, J. B. & Lilley, D. M. (1998) *Biochemistry* 37, 14195-14203.
17. Spratt, B. G., Hedge, P. J., te, H. S., Edelman, A. & Broome-Smith, J. K. (1986) *Gene* 41, 337-342.
18. Sioud, M. & Drlica, K. (1991) *Proc. Natl. Acad. Sci. U.S.A* 88, 7303-7307.
19. Murphy, J. C., Wibbenmeyer, J. A., Fox, G. E. & Willson, R. C. (1999) *Nat. Biotechnol.* 17, 822-823.
20. Murphy, J. C., Fox, G. E. & Willson, R. C. (2001) *Anal. Biochem.* in press.
21. Cline, J., Braman, J. C. & Hogrefe, H. H. (1996) *Nucleic Acids Res.* 24, 3546-3551.
22. Haupt, K., Roy, F. & Vijayalakshmi, M. A. (1996) *Anal. Biochem.* 234, 149-154.

All references, patents, patent application or articles, cited herein are incorporated by reference for all purposes permitted by controlling law and legal precedents. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for separating compounds comprising the steps of:

contacting a mixture comprising cell lysate or enzyme and a target polynucleotide compound which includes at least four non-shielded purine or pyrimidine moieties, and other compounds, with a solid composition including immobilized metal ions capable of binding compounds containing a non-shielded purine or pyrimidine moiety, to form a liquid product containing a reduced amount of the target polynucleotide; and exposing the solid composition to an elutant which selectively elutes the polynucleotide target compound; and collecting the target compound substantially free from both protein contaminants and histidine tags.

2. The method of claim 1, further comprising the step of: separating the liquid from the solid composition.

3. A method for separating compounds comprising the steps of:

passing a mixture of compounds including target polynucleotides comprising at least four non-shielded purine moieties, at least four non-shielded pyrimidine moieties, or mixtures thereof, through a column comprising an IMAC ligand, wherein the ligand is capable of differentially binding the polynucleotides; and eluting and collecting purified samples of the target polynucleotides substantially free from both protein contaminants and histidine tags.

4. The method of claim 3, further comprising the step of:

detecting each polynucleotide in an effluent from the column as a function of time from at least one detectable property associated with each compound; and determining the identity of each compound from the detected properties.

5. A method for purifying a lysate or enzyme product comprising a crude DNA or RNA target compound containing at least four non-shielded purine and/or pyrimidine base moieties, said method comprising the steps of: forming a crude mixture comprising a target compound and contaminants; contacting the crude mixture with an agent including an IMAC ligand capable of binding to the target compound to form an IMAC ligand complex;

separating the complex from the contaminants; and recovering the target compound from the complex substantially free from both protein contaminants and histidine tags.

6. A method for separating compounds comprising the step of:

contacting a mixture comprising cell lysate or enzyme and a target polynucleotide including a non-shielded purine or pyrimidine moiety and a compound including a shielded purine or pyrimidine moiety with a solid composition including immobilized metal ions capable of binding compounds containing a non-shielded purine or pyrimidine moiety to form a supernatant liquid having a reduced amount of compounds including a non-shielded purine or pyrimidine moiety;

wherein the compound including a non-shielded purine or pyrimidine moiety comprises a single stranded nucleic acid oligomer, or a single stranded nucleic acid polymer and the compounds including a shielded purine or pyrimidine moiety comprise double stranded nucleic acid oligomers or double stranded nucleic acid polymers;

wherein the supernatant liquid contains less than or equal to 5% by weight compounds comprising a non-shielded purine or pyrimidine moiety and the solid composition is substantially free from both protein contaminants and histidine tags.

7. A method of claim 6 wherein the mixture comprises poly(A) tailed mRNA sequences and other mRNA sequences from eukaryotic cells, the poly(a) mRNA sequences elute after the other mRNA sequences; or wherein the mixture of compounds comprises denatured nucleic acid sequences, wherein sequences having A-rich regions elute after sequences having T-rich regions, so that complementary strands can be resolved.

8. A method of claim 6 wherein the solution comprises denatured nucleic acid sequences, wherein sequences having C rich regions elute after sequences having G-rich regions so that complementary strands can be resolved; or wherein the mixture of compounds comprises denatured or partially denatured nucleic acid sequences having A-C, A-G, A-C-G, T-G, T-C and or T-G-C rich regions wherein the sequences having the A-C, A-G, and/or A-C-G rich regions elute after their complementary sequences having T-G, T-C and or T-G-C rich regions resulting in a resolution of complementary sequences.

9. The method of claim 1 wherein the target compound containing at least four non-shielded purine or pyrimidine moieties, is selected from the group consisting of single-stranded DNA, partially single-stranded DNA, denatured DNA, fragmented DNA or RNA, plasmid DNA containing single-stranded regions, incomplete or imperfect PCR products, chain-terminated polymerase products, restriction endonuclease-digested DNA, single-stranded PNA, single-stranded primer, single stranded RNA, poly A mRNA and messenger RNA, and is removed from compounds that do not contain a non-shielded purine or pyrimidine moiety.

10. A method for separating compounds comprising the step of: contacting a mixture comprising cell lysate or enzyme comprising double-stranded DNA and additionally comprising RNA and/or DNA, said RNA and/or DNA containing single-stranded portions having a non-shielded purine or pyrimidine moiety, with a solid composition comprising immobilized metal ions capable of binding compounds having a non-shielded purine or pyrimidine moiety, to form a supernatant liquid having a reduced amount of RNA and/or DNA having single-stranded portions and a solid composition substantially free from both protein contaminants and histidine tags.

11. A method according to claim 10 further comprising the steps of:

separating the supernatant liquid from the solid composition; or further comprising the steps of:

separating the supernatant liquid from the solid composition and eluting the RNA and/or DNA including a non-shielded purine or pyrimidine moiety from the solid composition.

12. A method of claim 11 wherein the supernatant liquid comprises compounds including a shielding purine or pyrimidine moiety having less than or equal to 1% by weight of compounds which include a non-shielded purine or pyrimidine moiety.

13. A method of claim 11 wherein the supernatant liquid comprises compounds including a shielded purine or pyrimidine moiety having less than or equal to 0.01% by weight compounds which include a non-shielded purine or pyrimidine moiety.

14. A method for separating compounds comprising the steps of: passing a solution comprising at least one polynucleotide, the polynucleotide containing single-stranded portions having at least four non-shielded purine or pyrimidine moieties through a column including an IMAC ligand, where the ligand is capable of differentially binding the polynucleotide without the presence of histidine tags;

and collecting purified samples of each polynucleotide compound substantially free from both protein contaminants and histidine tags.

15. The method of claim 14, further comprising the steps of: detecting each compound in an effluent from the column as a function of time from at least one detectable property associated with each compound; and determining the identity of each compound from the detected properties.

16. A method according to claim 9 wherein the target compound is separated from a compound selected from the group consisting of genomic DNA, double-stranded plasmid DNA, double-stranded PCR product, double-stranded hybrid and double-stranded PNA.

17. The method of claim 14, further comprising the step of: detecting each compound in an effluent from the column as a function of time from at least one detectable property associated with each compound.

18. The method of claim 1 wherein the contacting of the crude with the solid composition is performed in batch mode.

19. The method of claim 1 wherein the target compound comprises RNA having at least four non-shielded purine and/or pyrimidine moieties and is separated from a lysate containing double-stranded DNA.

20. The method of claim 1 wherein the target compound recovered from the solid composition is present in the original mixture at a concentration of less than 1 micromolar.

21. The method of claim 1 wherein the contacting of the mixture with the solid composition is performed in batch mode, and the target compound collected is present in the original mixture at a concentration of less than 1 micromolar.

22. The method of claim 1 wherein the solid composition comprises a ligand selected from the group consisting of iminodiacetic acid (IDA), nitrilotriacetic acid (NTA), pentadentate chelator (PDC), tris-(2-ethylaminoethyl) amine (TREN), dipicolyl amine (DPA) and chelating lipids.

23. A method of claim 1, wherein the target compound comprises DNA.

24. A method of claim 1, wherein the target compound comprises RNA.

25. A method of claim 1 wherein the target polynucleotide comprises single-stranded DNA, mRNA, miRNA, or denatured genomic DNA, and the other compounds comprise genomic DNA, plasmid DNA or PCR product DNA.

* * * * *

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial
<220> FEATURE:
<223> OTHER INFORMATION: PCT Primer Sequence
<220> FEATURE:
<221> NAME/KEY: misc_feature
<222> LOCATION: (1)..(23)
<223> OTHER INFORMATION: Forward PCT Primer Sequence 5' to 3'

<400> SEQUENCE: 1
taattgttgc cgggaagcta gag                                              23

<210> SEQ ID NO 2
<211> LENGTH: 25
<212> TYPE: DNA
<213> ORGANISM: Artificial
<220> FEATURE:
<223> OTHER INFORMATION: PCT Primer Sequence
<220> FEATURE:
<221> NAME/KEY: misc_feature
<222> LOCATION: (1)..(25)
<223> OTHER INFORMATION: Reverse PCR primer 5' to 3'

<400> SEQUENCE: 2
tcgcattgaa ttatgtgctg tgtag                                            25

<210> SEQ ID NO 3
<211> LENGTH: 20
<212> TYPE: DNA
<213> ORGANISM: Artificial
<220> FEATURE:
<223> OTHER INFORMATION: Synthetic Oligonucleotide Sequence

<400> SEQUENCE: 3
cagacgatag tcctagttgc                                                  20

<210> SEQ ID NO 4
<211> LENGTH: 20
<212> TYPE: DNA
<213> ORGANISM: Artificial
<220> FEATURE:
<223> OTHER INFORMATION: Synthetic Oligonucleotide Sequence

<400> SEQUENCE: 4
```

```
gtctgctatc aggatcaacg                                                    20

<210> SEQ ID NO 5
<211> LENGTH: 20
<212> TYPE: DNA
<213> ORGANISM: Artificial
<220> FEATURE:
<223> OTHER INFORMATION: Synthetic Oligonucleotide Sequence

<400> SEQUENCE: 5
aaaaaaaaaa aaaaaaaaaa                                                    20

<210> SEQ ID NO 6
<211> LENGTH: 20
<212> TYPE: DNA
<213> ORGANISM: Artificial
<220> FEATURE:
<223> OTHER INFORMATION: Synthetic Oligonucleotide Sequence

<400> SEQUENCE: 6
tttttttttt tttttttttt                                                    20

<210> SEQ ID NO 7
<211> LENGTH: 20
<212> TYPE: DNA
<213> ORGANISM: Artificial
<220> FEATURE:
<223> OTHER INFORMATION: Synthetic Oligonucleotide Sequence

<400> SEQUENCE: 7
cccccccccc cccccccccc                                                    20

<210> SEQ ID NO 8
<211> LENGTH: 20
<212> TYPE: DNA
<213> ORGANISM: Artificial
<220> FEATURE:
<223> OTHER INFORMATION: Synthetic Oligonucleotide Sequence

<400> SEQUENCE: 8
gggggggggg gggggggggg                                                    20
```